(12) United States Patent
Eversull et al.

(10) Patent No.: US 8,388,628 B2
(45) Date of Patent: Mar. 5, 2013

(54) EXPANDABLE SHEATH FOR DELIVERING INSTRUMENTS AND AGENTS INTO A BODY LUMEN AND METHODS FOR USE

(75) Inventors: Christian S. Eversull, Palo Alto, CA (US); Nicholas J. Mourlas, Mountain View, CA (US); Stephen A. Leeflang, Sunnyvale, CA (US)

(73) Assignee: Medtronic, Inc., Minneapolis, MN (US)

( * ) Notice: Subject to any disclaimer, the term of this patent is extended or adjusted under 35 U.S.C. 154(b) by 1787 days.

(21) Appl. No.: 10/934,305

(22) Filed: Sep. 2, 2004

(65) Prior Publication Data

US 2005/0085841 A1      Apr. 21, 2005

Related U.S. Application Data

(60) Provisional application No. 60/500,202, filed on Sep. 4, 2003.

(51) Int. Cl.
*A61B 17/00* (2006.01)

(52) U.S. Cl. .................. 606/108; 604/102.03; 606/159; 606/194

(58) Field of Classification Search .................. 606/190, 606/198, 192, 194, 108, 159; 604/102.03
See application file for complete search history.

(56) References Cited

U.S. PATENT DOCUMENTS

| | | | |
|---|---|---|---|
| 4,392,853 A | 7/1983 | Muto | |
| 4,401,433 A | 8/1983 | Luther | |
| 4,406,656 A | 9/1983 | Hattler et al. | |
| 4,451,256 A | 5/1984 | Weikl et al. | |
| 4,569,347 A | 2/1986 | Frisbie | |
| 4,601,713 A | 7/1986 | Fuqua | |
| 4,710,181 A | 12/1987 | Fuqua | |
| 4,738,666 A | 4/1988 | Fuqua | |
| 4,774,949 A * | 10/1988 | Fogarty | 606/108 |
| 4,921,479 A | 5/1990 | Grayzel | |
| 5,015,239 A | 5/1991 | Browne | |
| 5,201,756 A | 4/1993 | Horzewski et al. | |
| 5,209,728 A | 5/1993 | Kraus et al. | |
| 5,234,425 A | 8/1993 | Fogarty et al. | |
| 5,254,084 A | 10/1993 | Geary et al. | |

(Continued)

FOREIGN PATENT DOCUMENTS

| | | |
|---|---|---|
| WO | WO 84/01512 | 4/1984 |
| WO | WO 98/29026 | 7/1998 |

(Continued)

OTHER PUBLICATIONS

USPTO Office Action for co-pending U.S. Appl. No. 10/423,321 dated Oct. 24, 2006.

(Continued)

*Primary Examiner* — S. Thomas Hughes
*Assistant Examiner* — Julie A Szpira

(57) ABSTRACT

Apparatus and methods are provided for delivering a guidewire, agents, and the like through an occlusion in a body vessel or other body lumen. The apparatus includes a flexible catheter or other elongate member including a proximal end, a distal end sized for insertion into a body lumen, and a first lumen extending from the proximal end to a distal region of the tubular member. An expandable sheath is provided on the distal region of the catheter that is expandable from a contracted condition to minimize a profile of the sheath to allow insertion along with the tubular member into a body lumen, to an enlarged condition wherein the sheath at least partially defines a lumen communicating with and extending distally from the first lumen of the tubular member.

2 Claims, 18 Drawing Sheets

U.S. PATENT DOCUMENTS

| | | | |
|---|---|---|---|
| 5,256,150 A | | 10/1993 | Quiachon et al. |
| 5,263,932 A | | 11/1993 | Jang |
| 5,267,958 A | * | 12/1993 | Buchbinder et al. ..... 604/103.14 |
| 5,304,134 A | | 4/1994 | Kraus et al. |
| 5,395,349 A | | 3/1995 | Quiachon et al. |
| 5,413,560 A | | 5/1995 | Solar |
| 5,431,676 A | | 7/1995 | Dubrul et al. |
| 5,468,225 A | * | 11/1995 | Teirstein ................. 604/103.04 |
| 5,472,418 A | | 12/1995 | Palestrant |
| 5,549,556 A | * | 8/1996 | Ndondo-Lay et al. ..... 604/103.1 |
| 5,573,517 A | | 11/1996 | Bonutti et al. |
| 5,618,267 A | | 4/1997 | Palestrant |
| 5,674,240 A | | 10/1997 | Bonutti et al. |
| 5,735,831 A | | 4/1998 | Johnson et al. |
| 5,749,889 A | * | 5/1998 | Bacich et al. ................. 606/198 |
| 5,762,604 A | | 6/1998 | Kieturakis |
| 5,772,628 A | * | 6/1998 | Bacich et al. ................... 604/43 |
| 5,795,331 A | * | 8/1998 | Cragg et al. ............. 604/103.01 |
| 5,810,776 A | | 9/1998 | Bacich et al. |
| 5,824,041 A | | 10/1998 | Lenker et al. |
| 5,827,227 A | | 10/1998 | DeLago |
| 5,911,702 A | | 6/1999 | Romley et al. |
| 5,944,691 A | | 8/1999 | Querns et al. |
| 5,961,499 A | | 10/1999 | Bonutti et al. |
| 5,997,508 A | | 12/1999 | Lunn et al. |
| 6,068,610 A | * | 5/2000 | Ellis et al. .................. 604/96.01 |
| 6,068,623 A | | 5/2000 | Zadno-Azizi et al. |
| 6,090,072 A | | 7/2000 | Kratoska et al. |
| 6,120,477 A | | 9/2000 | Campbell et al. |
| 6,179,827 B1 | | 1/2001 | Davis et al. |
| 6,183,443 B1 | | 2/2001 | Kratoska et al. |
| 6,197,016 B1 | | 3/2001 | Fourkas et al. |
| 6,312,406 B1 | | 11/2001 | Jayaraman |
| 6,338,730 B1 | | 1/2002 | Bonutti et al. |
| 6,361,528 B1 | | 3/2002 | Wilson et al. |
| 6,596,020 B2 | * | 7/2003 | Vardi et al. ................... 623/1.11 |
| 6,652,492 B1 | | 11/2003 | Bell et al. |
| 6,814,715 B2 | | 11/2004 | Bonutti et al. |
| 7,004,173 B2 | * | 2/2006 | Sparks et al. ................. 128/898 |
| 7,399,307 B2 | * | 7/2008 | Evans et al. .................... 606/194 |
| 2001/0039418 A1 | | 11/2001 | Schaer |
| 2001/0053919 A1 | | 12/2001 | Kieturakis et al. |
| 2002/0095117 A1 | | 7/2002 | Wilson et al. |
| 2002/0099431 A1 | | 7/2002 | Armstrong et al. |
| 2002/0165598 A1 | | 11/2002 | Wahr et al. |
| 2003/0065353 A1 | | 4/2003 | Horzewski et al. |
| 2003/0233115 A1 | | 12/2003 | Eversull et al. |
| 2004/0006344 A1 | | 1/2004 | Nguyen et al. |
| 2004/0073286 A1 | | 4/2004 | Armstrong et al. |
| 2004/0087968 A1 | | 5/2004 | Core |
| 2004/0097788 A1 | | 5/2004 | Mourlas et al. |

FOREIGN PATENT DOCUMENTS

WO            0103766 A      1/2001

OTHER PUBLICATIONS

USPTO Office Action for co-pending U.S. Appl. No. 10/934,082 dated Feb. 8, 2007.

* cited by examiner

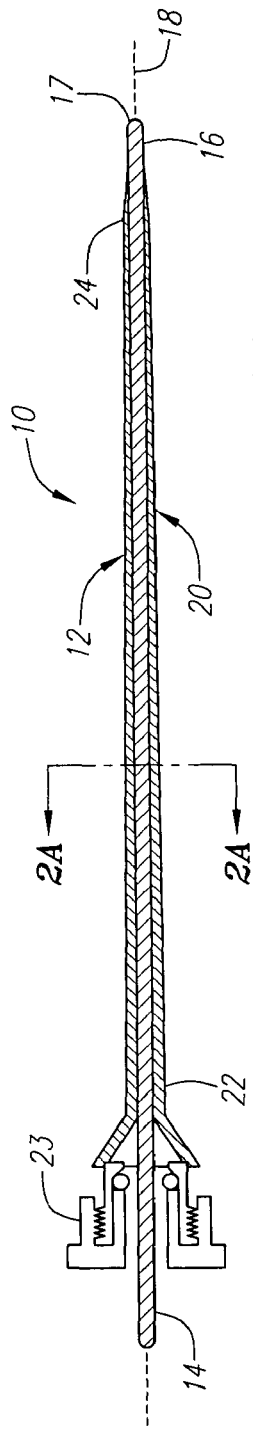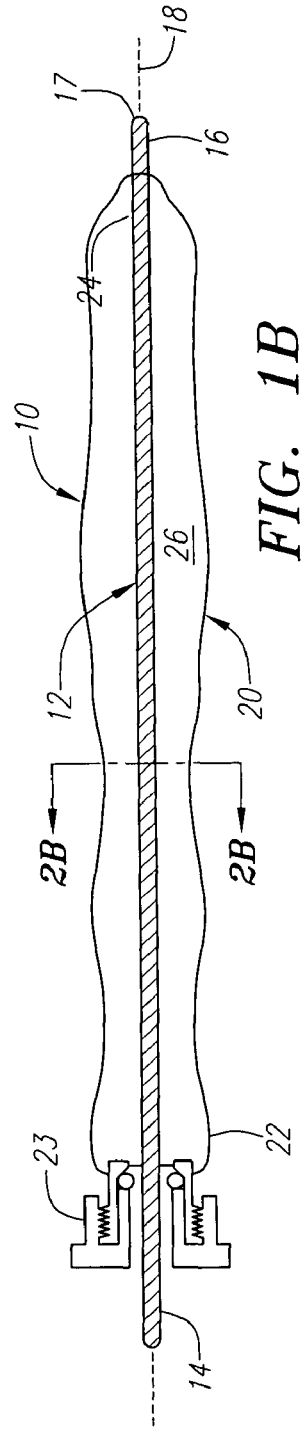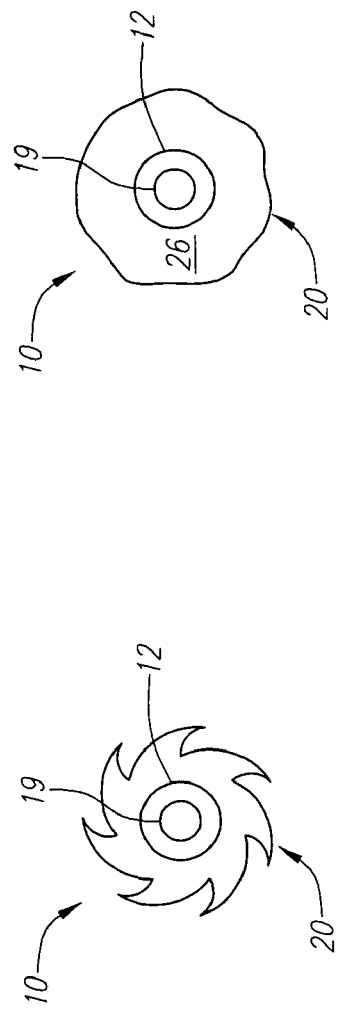
FIG. 1A
FIG. 1B
FIG. 2A
FIG. 2B

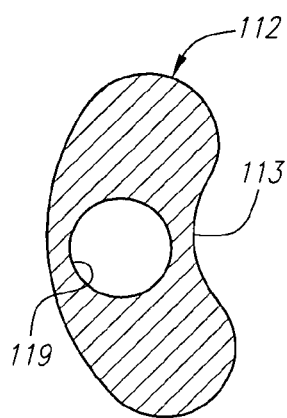
*FIG. 3A*
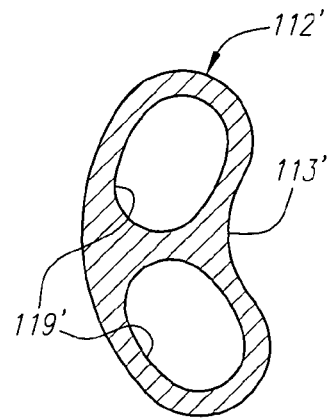
*FIG. 3B*
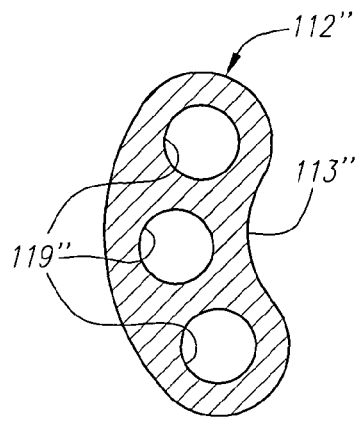
*FIG. 3C*
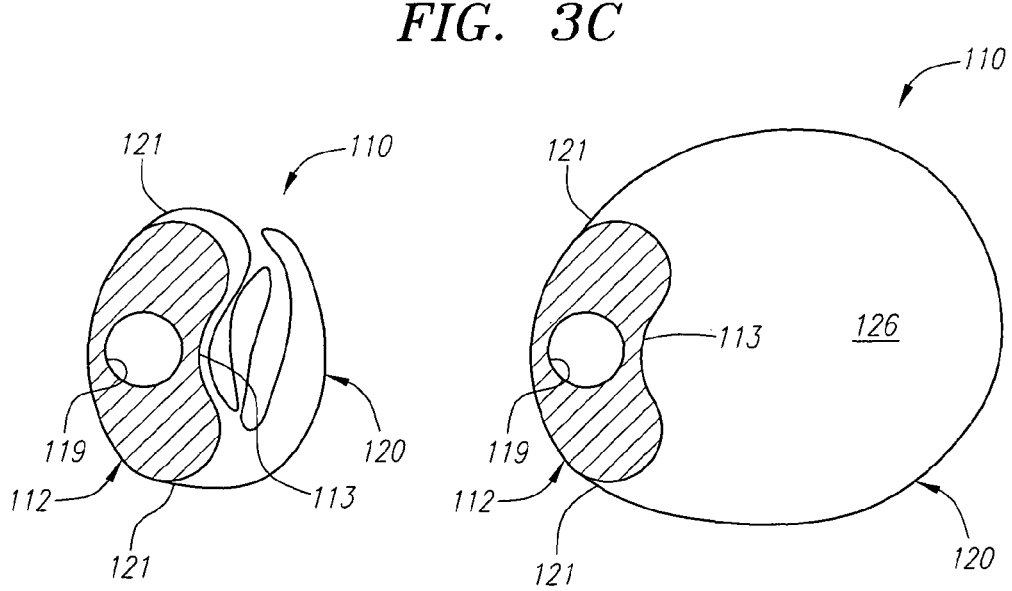
*FIG. 4A*          *FIG. 4B*

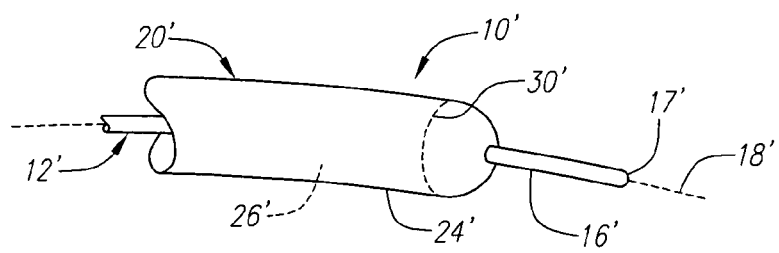
FIG. 5
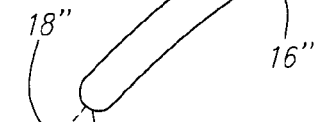
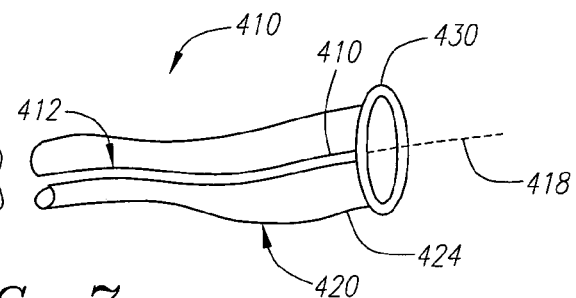
FIG. 6
FIG. 7
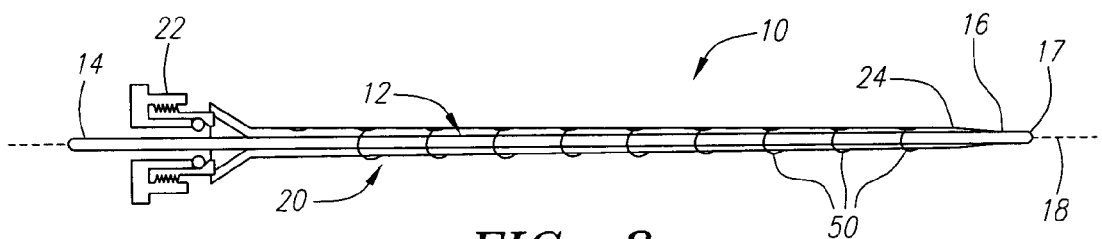
FIG. 8
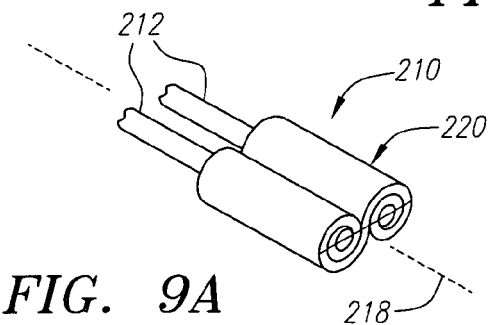
FIG. 9A
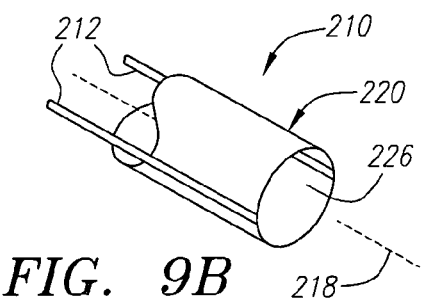
FIG. 9B

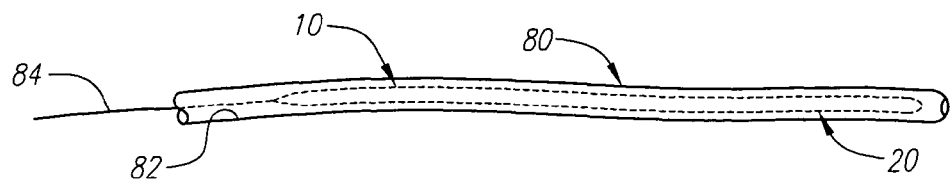
FIG. 13A
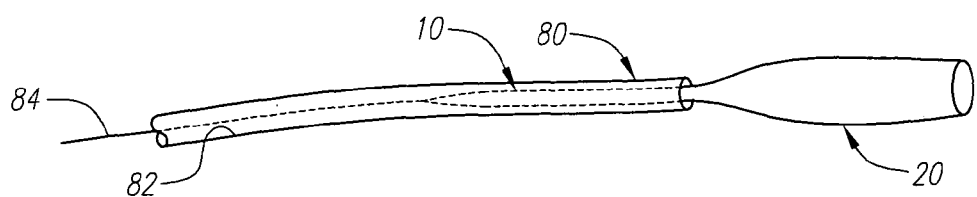
FIG. 13B
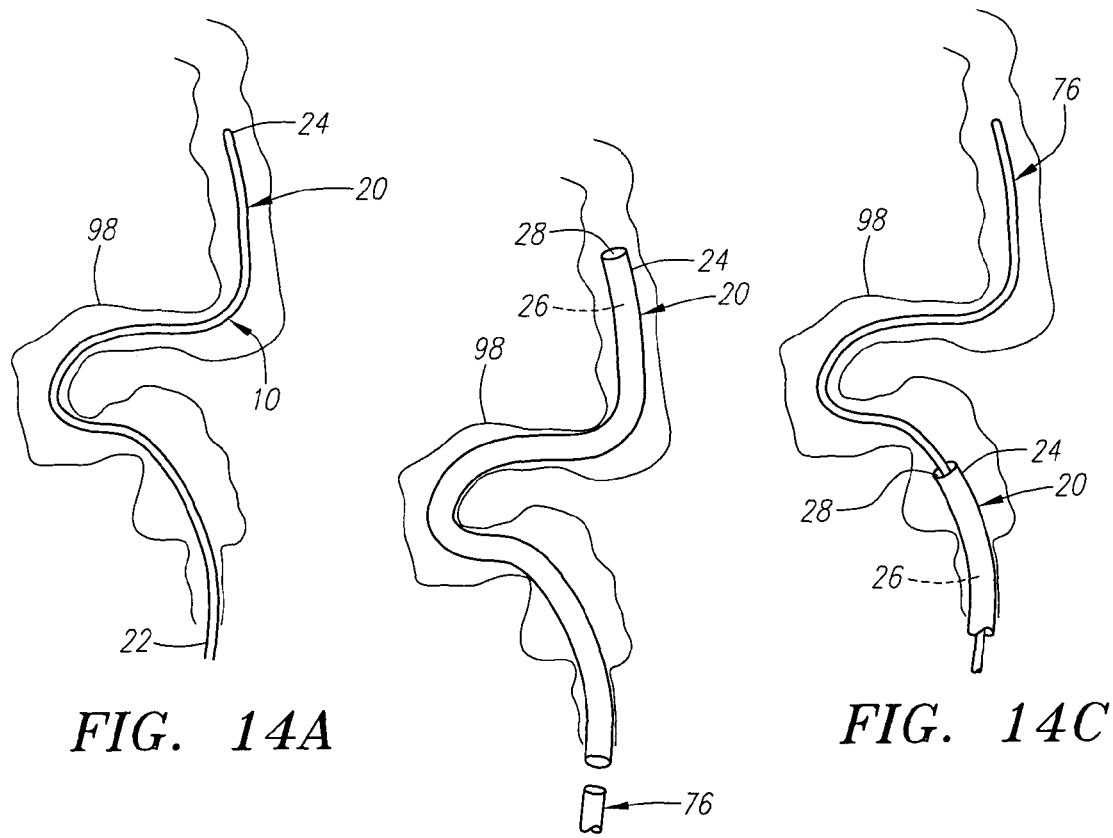
FIG. 14A
FIG. 14B
FIG. 14C

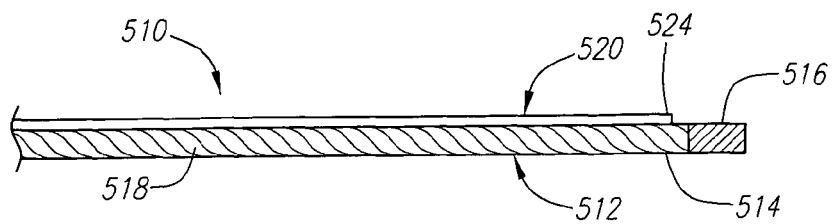
FIG. 18
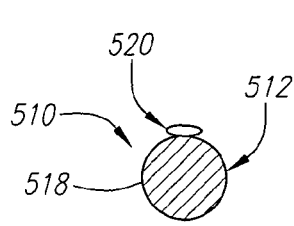 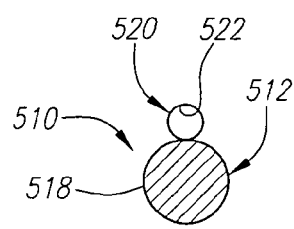 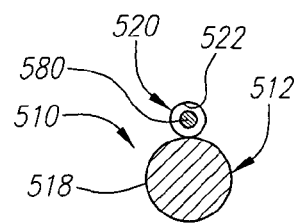
FIG. 19A     FIG. 19B     FIG. 19C
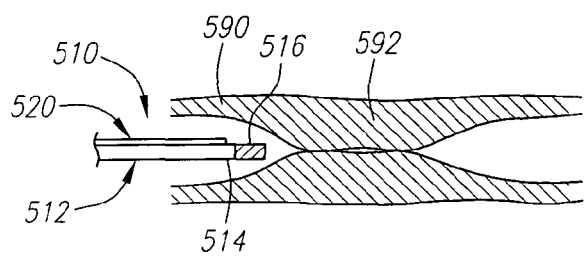
FIG. 20A
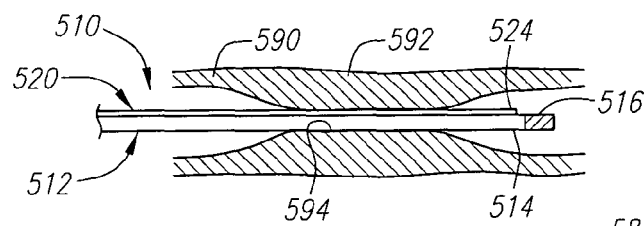
FIG. 20B
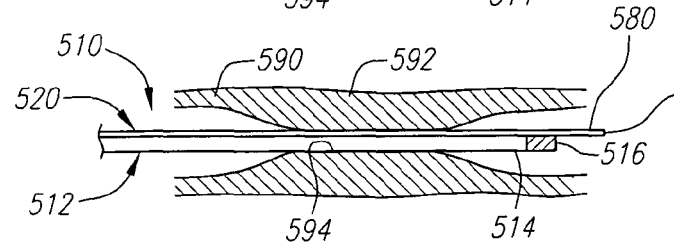
FIG. 20C
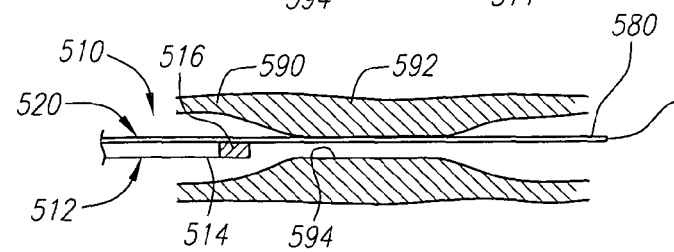
FIG. 20D

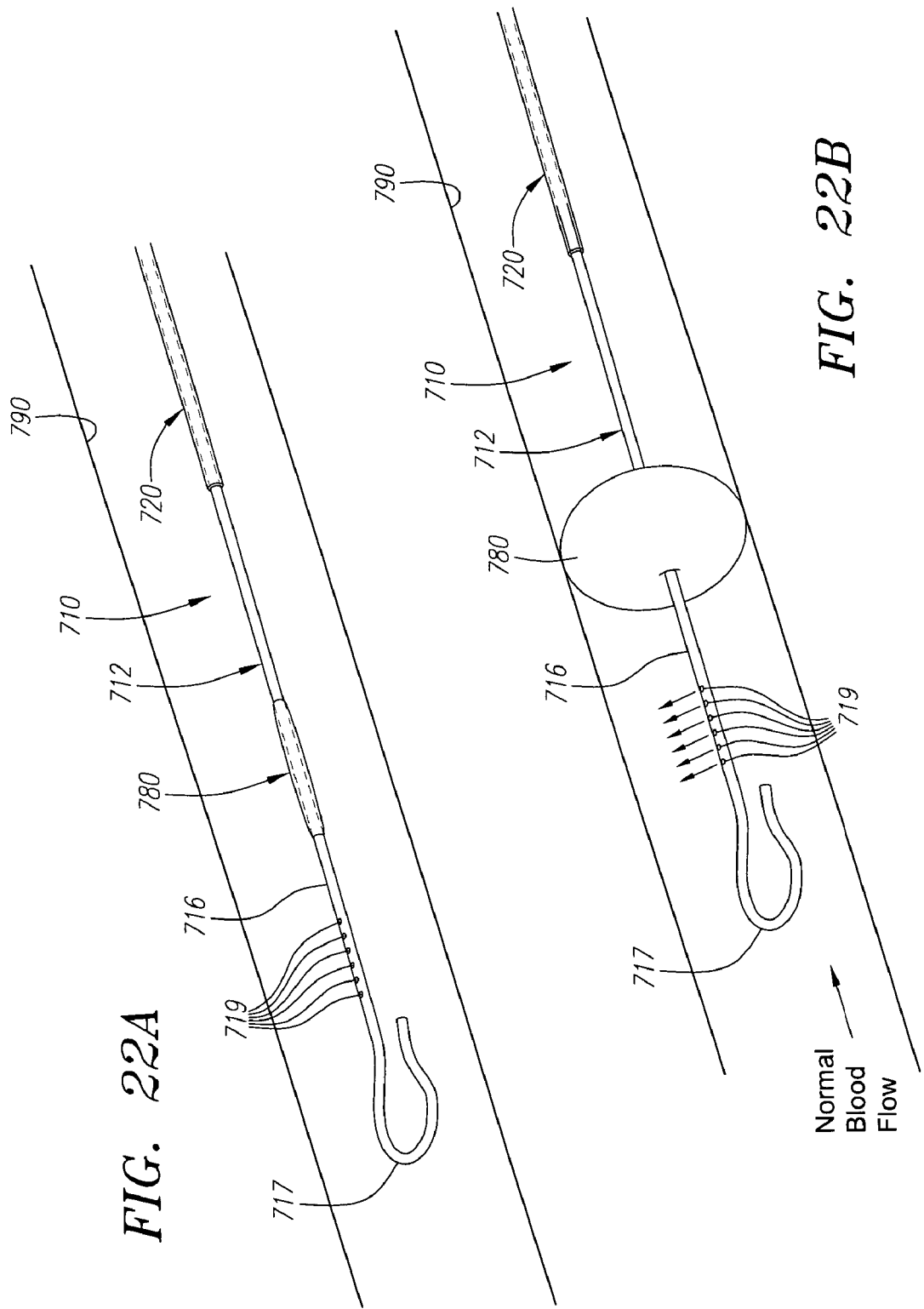

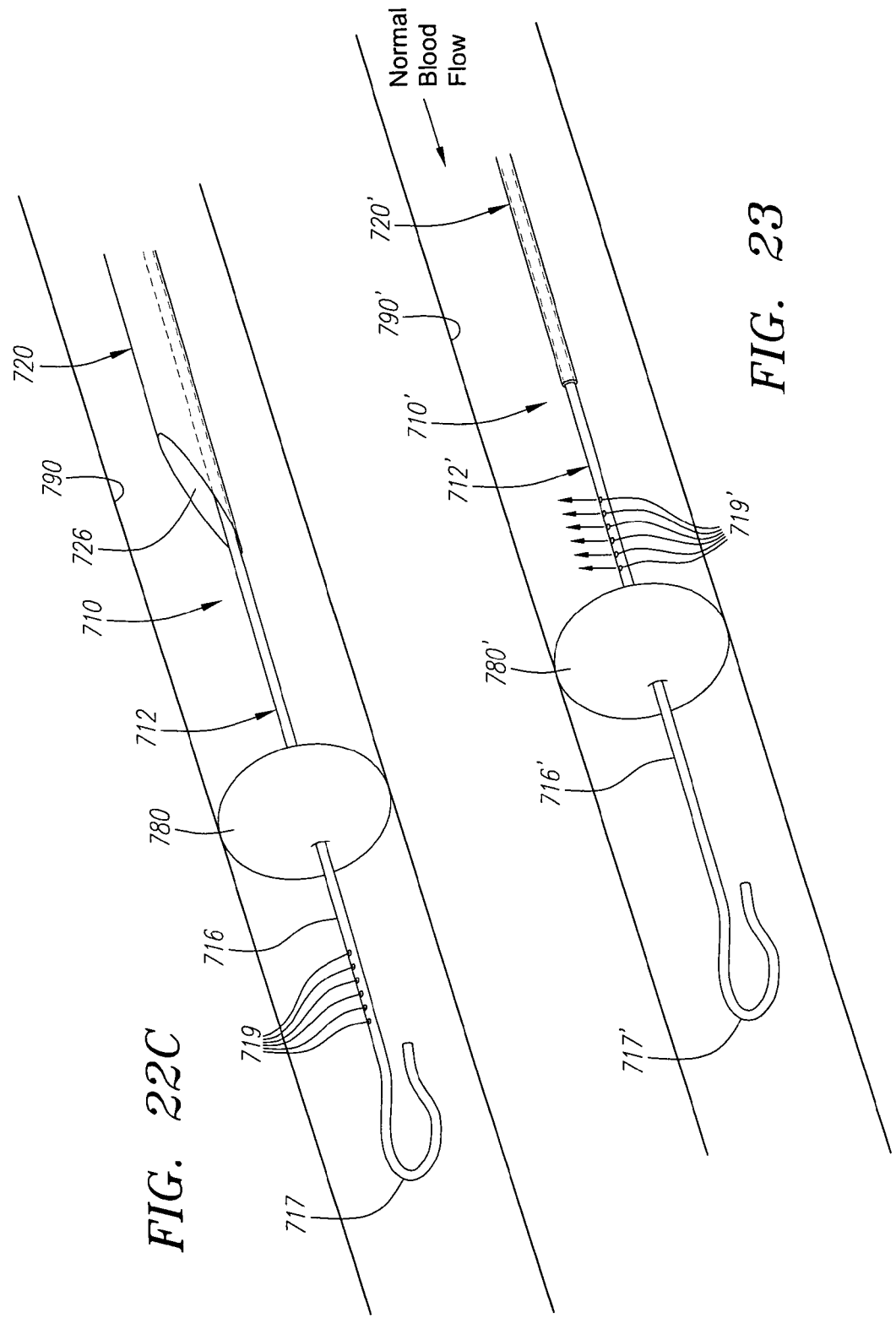

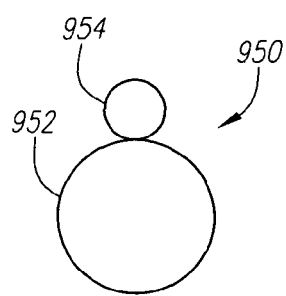
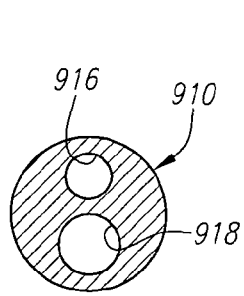
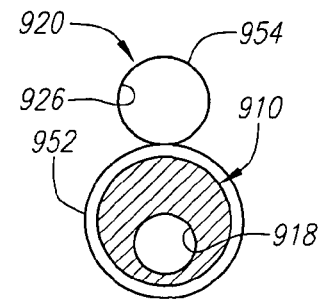
FIG. 27A     FIG. 27B     FIG. 27C
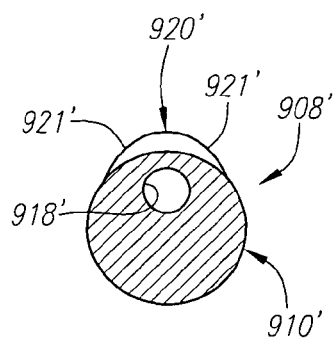
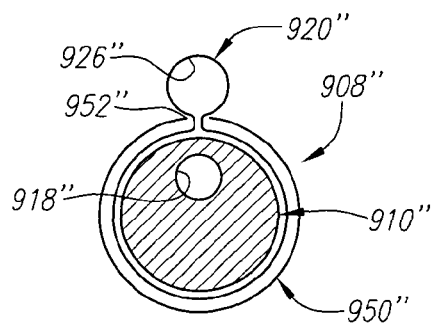
FIG. 28A          FIG. 28B
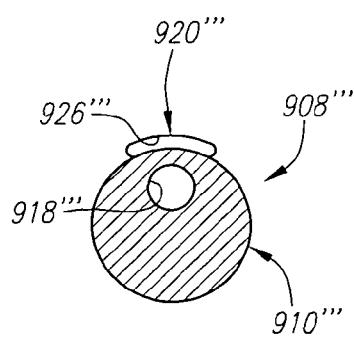
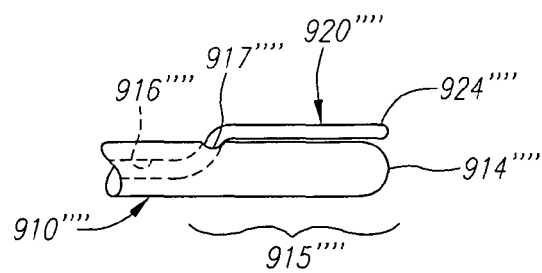
FIG. 28C          FIG. 28D

EXPANDABLE SHEATH FOR DELIVERING INSTRUMENTS AND AGENTS INTO A BODY LUMEN AND METHODS FOR USE This application claims benefit of provisional application Ser. No. 60/500,202, filed Sep. 4, 2003, the disclosure of which is hereby incorporated herein, by reference.

FIELD OF THE INVENTION

The present invention relates generally to apparatus and methods for delivering instruments and/or agents during a medical procedure, and, more particularly, to catheter devices and guide sheaths for accessing body lumens and/or delivering instruments into body lumens of a patient.

BACKGROUND

Minimally invasive procedures have been implemented in a variety of medical settings, e.g., for vascular interventions, such as angioplasty, stenting, embolic protection, electrical heart stimulation, heart mapping and visualization, and the like. These procedures generally rely on accurately navigating and placing instruments within a patient's vasculature.

During such procedures, a target vessel may be accessed using a guidewire advanced through the intervening vasculature into the target vessel, thereby providing a "railway" to the vessel. One or more instruments, e.g., catheters, sheaths, and the like, may be advanced over the guidewire or "rail" into the vessel. Thus, a diagnostic and/or therapeutic procedure may be performed by advancing one or more instruments over this railway.

There are many risks involved with advancing instruments over a guidewire. For example, a catheter or other instrument may skive or otherwise damage a wall of a vessel, particularly as the instrument passes through narrow passages or tortuous anatomy involving sharp bends. Such instruments also risk dislodging embolic material or even perforating the vessel wall.

In addition, it is often desirable to access very small vessels deep within the body, e.g., within a patient's heart, for example, to place a ventricular pacing lead within a coronary vein. However, the instrument(s), e.g., guide sheath, lead, etc., may have a relatively large cross-section and/or may have a relatively blunt distal tip, making it difficult to advance such instruments as deeply as desired into such small vessels.

Accordingly, apparatus and methods for delivering instruments into blood vessels or other body lumens and/or for otherwise accessing vessels or other body lumens would be useful.

SUMMARY OF THE INVENTION

The present invention is directed generally to apparatus and methods for providing access to body lumens and/or for delivering instruments and/or agents into body lumens during a medical procedure. More particularly, the present invention is directed to catheters and guide sheaths, and to methods for using them to facilitate delivering instruments and/or agents into body lumens of a patient, e.g., within the patient's coronary, neuro, and/or peripheral vasculature, within the patient's gastrointestinal tract, urogenital tract, respiratory tract, lymphatic system, and/or within surgically created passages.

In accordance with one embodiment, a sheath apparatus is provided that includes an elongate expandable sheath that may be expandable from a contracted condition to minimize a profile of the sheath, e.g., to allow insertion into a body lumen, to an enlarged condition wherein the sheath at least partially defines a lumen therein. The sheath may be formed from a lubricious material, a polymer, and/or an elastomeric material, preferably having a relatively thin wall, thereby providing a tubular sheath that may be substantially flexible and/or flimsy. For example, the sheath may include a wall thickness between about 0.001-1.25 millimeter, and preferably between about 0.005-0.06 millimeter.

Optionally, the sheath may include one or more reinforcing elements extending along the sheath, e.g., axially, helically, and/or circumferentially around the sheath. Such reinforcing elements may support the sheath during delivery and/or may enhance the sheath assuming a desired shape and/or size in the enlarged condition. In addition or alternatively, a stiffening or reinforcing member may be provided for supporting or otherwise carrying the sheath to facilitate its introduction in the contracted condition. In another alternative, the expandable sheath may be carried on a distal end of a catheter or other tubular member. Optionally, the sheath and/or stiffening member(s) may be coated, e.g., with an anti-thrombotic agent and/or hydrophilic coating.

In accordance with still another embodiment, a method is provided for performing a procedure at a location within a body lumen of a patient. An expandable sheath may be advanced from an entry site into the body lumen with the sheath in a contracted condition. The sheath may be expanded to an enlarged condition, thereby defining a lumen within the sheath, and a distal protection element may be deployed beyond a distal end of the sheath adjacent the location. A diagnostic and/or therapeutic procedure may be performed within the body lumen via the lumen defined by the sheath, the distal protection element preventing embolic material from leaving the location. Upon completing the procedure, the sheath and distal protection element may be removed from the body lumen.

In accordance with yet another embodiment, a method is provided for accessing a body lumen of a patient. The body lumen may be, for example, a vessel or other passage within a patient's urogenital tract, respiratory tract, gastrointestinal tract, lymphatic system, or vascular system. In addition or alternatively, the body lumen may be a passage surgically created within the patient, e.g., an interstitial space accessed via a surgically-created entry site.

Generally, an expandable sheath is advanced from an entry site to a body lumen with the sheath in a contracted condition. The sheath may be advanced over a guide wire or in conjunction with another rail. Preferably, the sheath is advanced from the entry site until a distal end of the sheath is disposed within the body lumen while a proximal end of the sheath remains outside the entry site.

Once the sheath reaches the target body lumen, the sheath may be expanded to an enlarged condition, thereby defining a lumen within the sheath, e.g., that extends from the entry site to the target body lumen. The sheath may be expanded to the enlarged condition, e.g., by introducing a fluid into the lumen defined by the sheath, such as saline, contrast, carbon dioxide, oxygen, and/or air, and/or by introducing an instrument into the lumen defined by the sheath.

A diagnostic and/or therapeutic procedure may be performed within the body lumen via the lumen defined by the sheath. In one embodiment, the entry site may be a percutaneous site communicating with the patient's vasculature, and the body lumen may be a blood vessel, e.g., within the patient's coronary, peripheral, or neuro vasculature. The procedure may include introducing one or more instruments or agents through the lumen defined by the sheath into the target blood vessel, e.g., a catheter, a guidewire, a balloon, a stent, a filter, a pacing lead, an atherectomy device, a thrombectomy device, and/or a medicament (e.g., anti-inflammatory drug, anti-thrombotic agent, inhibitors, and the like). In a preferred embodiment, the target blood vessel may be a stenotic or occluded region within an artery. In another preferred embodiment, the target blood vessel may be a coronary vein, and the one or more instruments may include an electrical lead.

Upon completing the procedure, the sheath may be removed from the body lumen. Optionally, the sheath may be at least partially collapsed from the enlarged condition before removing the sheath from the body lumen, e.g., by creating a vacuum within the sheath and/or by withdrawing the sheath into a catheter or other tubular member. Alternatively, the sheath may be split along a single longitudinal seam, or along two or more seams into two or more pieces to facilitate removal from the body lumen.

In accordance with another embodiment, an apparatus is provided for delivering an instrument, e.g., a guidewire, into a body lumen of a patient, e.g., across a total occlusion within a blood vessel. The apparatus generally includes a catheter or other elongate and/or tubular member including proximal and distal ends, and an expandable sheath attached to an outer surface of the catheter. The sheath, e.g., a flexible and/or flimsy tubular member and/or sheet, may be expandable from a contracted condition to minimize a profile of the sheath, and an enlarged condition wherein the sheath at least partially defines an accessory lumen extending between proximal and distal ends of the sheath.

In one embodiment, the expandable sheath is provided on a distal region of the catheter or may extend between the proximal and distal ends of the catheter.

In accordance with yet another embodiment, a method is provided for delivering an instrument through an occlusion in a body lumen using a catheter or other elongate member including an expandable sheath extending along an outer surface of the elongate member. A distal end of the catheter may be introduced into the body lumen proximal to the occlusion with the sheath in a contracted condition. The distal end of the catheter may be advanced through the occlusion until a distal end of the sheath is disposed distal to the occlusion. The distal end of the catheter may include one or more elements for facilitating advancing the distal end through the occlusion, e.g., an imaging element, a dissection element, and/or a steering element.

An instrument, e.g., a guidewire or other elongate member, may be advanced through the sheath until a distal end of the instrument is disposed distal to the occlusion. The sheath may be expanded before inserting the instrument, e.g., by introducing fluid into the lumen of the sheath, or the sheath may be expanded as the instrument is inserted into the sheath.

The catheter and sheath may then be withdrawn from the body lumen, e.g., leaving the guidewire or other elongate member across the occlusion. One or more instruments may be advanced over the guidewire, e.g., after the catheter is withdrawn to observe and/or treat the occlusion.

In accordance with still another embodiment, an apparatus is provided for delivering a guidewire through an occlusion in a body lumen that includes a catheter or other elongate member including a proximal end, a distal end sized for insertion into a body lumen, and a first lumen extending from the proximal end to a distal region of the tubular member. An expandable sheath is provided on the distal region of the elongate member, the sheath being expandable from a contracted condition to minimize a profile of the sheath, to an enlarged condition wherein the sheath at least partially defines a lumen communicating with the first lumen of the tubular member.

In accordance with yet another embodiment, an apparatus is provided for delivery into a body lumen of a patient that includes a flexible catheter including a proximal end, and a distal end sized for insertion into a body lumen, and an expandable sheath attached around an outer surface of the catheter. The sheath may be expandable from a contracted condition to minimize a profile of the sheath, to an enlarged condition wherein at least a portion of the sheath moves away from the outer surface of the catheter to at least partially define an accessory lumen extending between the proximal and distal ends of the sheath.

Other aspects and features of the present invention will become apparent from consideration of the following description taken in conjunction with the accompanying drawings.

BRIEF DESCRIPTION OF THE DRAWINGS

FIGS. 1A and 1B are partial cross-sectional side views of a first preferred embodiment of a sheath apparatus, including an expandable sheath and a stiffening member, showing the sheath in contracted and expanded conditions, respectively.

FIGS. 2A and 2B are cross-sections of the apparatus of FIGS. 1A and 1B taken along lines 2A and 2B, respectively.

FIGS. 3A-3C are alternate cross-sections of a stiffening member that may be incorporated into a sheath apparatus.

FIGS. 4A and 4B are cross-sectional views of an alternative embodiment of a sheath apparatus, including an expandable sheath attached to a stiffening member, such as that shown in FIG. 3A, showing the sheath in contracted and expanded conditions, respectively.

FIG. 5 is a perspective detail of a distal end of a sheath apparatus, including an expandable sheath having a weakened region for creating an opening in a wall thereof.

FIG. 6 is a perspective detail of an alternative distal end of a sheath apparatus, including an expandable sheath including a beveled distal end having an opening therein.

FIG. 7 is a side view of an alternative embodiment of a sheath apparatus, including an expandable sheath with an inflatable cuff on one end.

FIG. 8 is a partial cross-sectional side view of a sheath apparatus including wire loops wrapped around an expandable sheath to constrain the sheath in a contracted condition.

FIGS. 9A and 9B are perspective details of a sheath apparatus, showing an expandable sheath in contracted and expanded conditions, respectively.

FIGS. 13A and 13B are side views of another embodiment of a sheath apparatus including a tubular constraint from which the apparatus may be deployed.

FIGS. 14A-14C are partial cross-sectional views of a patient's colon, showing a method for delivering a colonoscope using a sheath apparatus, in accordance with the present invention.

FIG. 18 is a side view of another embodiment of an apparatus including a catheter and an expandable sheath, in accordance with the present invention.

FIGS. 19A-19C are cross-sections of the apparatus of FIG. 18, showing the sheath contracted, expanded, and with a guidewire therein, respectively.

FIGS. 20A-20D are cross-sectional views of a blood vessel, showing a method for delivering a guidewire across an occlusion in the vessel.

FIGS. 22A-22C are cross-sectional views of a blood vessel, showing a method for delivering fluid upstream from an occlusion balloon of a sheath apparatus, in accordance with the present invention.

FIG. 23 is a cross-sectional view of a blood vessel, showing an alternative method for delivering fluid upstream from an occlusion balloon of a sheath apparatus.

FIGS. 27A-27C are cross-sections of the catheter and sheath of FIGS. 25A-25C, showing a method for making and assembling the catheter and sheath.

FIGS. 28A-28C are cross-sectional views showing alternative embodiments of the catheter and sheath of FIGS. 25A-25C.

FIG. 28D is a side view of a distal end of another alternative of a catheter including an expandable sheath in an enlarged condition.

DETAILED DESCRIPTION OF THE PREFERRED EMBODIMENTS

Figure 10A:
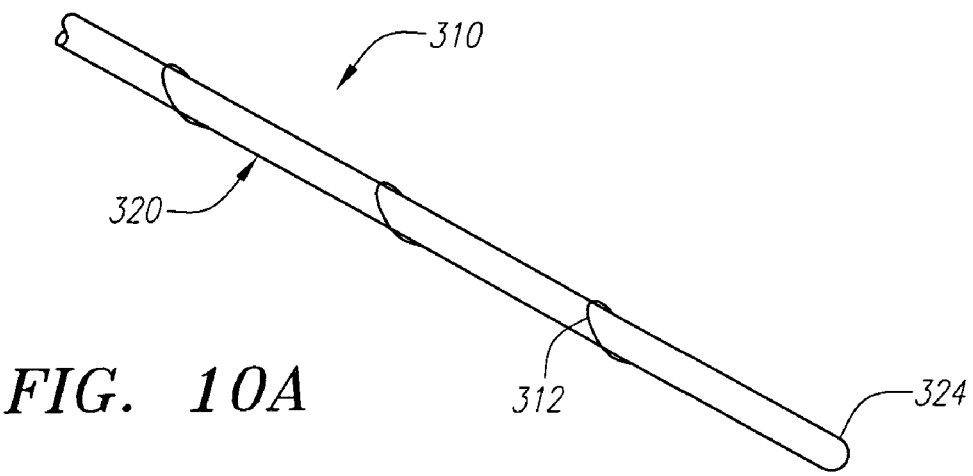
FIGS. 10A and 10B are perspective details of another embodiment of a sheath apparatus, showing an expandable sheath in contracted and expanded conditions, respectively.

Turning to the drawings, FIGS. 1A-2B show a first preferred embodiment of an apparatus 10 for providing access within a body lumen (not shown) and/or for delivering one or more instruments (also not shown) within a body lumen, such as a vessel within a patient's vasculature, a passage within a patient's gastrointestinal tract, urogenital tract, respiratory tract, lymphatic system, and the like.

Generally, the apparatus 10 includes a flexible elongate stiffening member 12 providing a "backbone" for the apparatus 10, and an expandable membrane or sheath 20. The stiffening member 12 includes a proximal end 14 and a distal end 16 defining a longitudinal axis 18 therebetween. In addition, the stiffening member 12 may have sufficient length to be advanced from a location outside a patient's body (not shown) through any intervening body passages into a site to be accessed and/or treated. The distal end 16 may have a size and/or shape for insertion into a body lumen, e.g., including a rounded or other substantially atraumatic distal tip 17, a "J" tip (not shown), and the like.

In one embodiment, the stiffening member 12 may be a solid or hollow guidewire, a catheter, a thread, and the like. Preferably, the stiffening member 12 is substantially flexible to facilitate advancement through tortuous anatomy without causing dissection or perforation, yet has sufficient column strength and/or torque-ability that the distal end 16 may be advanced through a body lumen by pushing the proximal end 14 without substantial risk of kinking and/or buckling. The stiffening member 12 may include one or more lumens 19 (shown in FIGS. 2A and 2B) extending between the proximal and distal ends 14, 16, e.g., to allow fluids to be delivered therethrough and/or to receive a guide wire or other instrument (not shown) therethrough.

The stiffening member 12 may have a substantially symmetrical cross-section, e.g., a cylindrical cross-section, as shown in FIGS. 2A and 2B, or may have an asymmetrical cross-section, e.g., an arcuate cross-section, as shown in FIGS. 3A-4B. In the embodiments shown in FIGS. 3A-4B, the stiffening member 112 may define a groove 113 extending at least partially between its proximal and distal ends (not shown in FIGS. 3A-4B).

The stiffening member 12 or 112 may be formed from a variety of materials and using various methods known in the art. For example, the stiffening member may be formed from plastic, glass, composite, and/or metal using known methods, such as extrusion and the like, thereby providing a desired combination of flexibility and column strength. As used herein, the terms "backbone," "backbone member," or "stiffening member" may include any elongate flexible structure capable of supporting or reinforcing an expandable membrane or other sheath to facilitate introducing the sheath into a body lumen of a patient and/or to facilitate tracking a secondary device along the axis of the sheath and/or over the entire apparatus. The stiffening member 12 may have a diameter or other maximum cross-section between about 0.05-5 millimeters, and preferably between about 0.2-2 millimeters.

Returning to FIGS. 1A and 1B, the expandable membrane or sheath 20 includes a proximal end 22, a distal end 24, and one or more side walls extending between the proximal and distal ends 22, 24, thereby at least partially defining a lumen 26. As used herein, the term "sheath" or "guide sheath" may include any structure that at least partially defines a lumen, whether the structure is substantially tubular or only partially defines the lumen.

The sheath 20 may be expandable from a contracted condition, as shown in FIGS. 1A and 2A, to an enlarged condition, as shown in FIGS. 1B and 2B. When the sheath 20 is in a contracted condition, the apparatus 10 may assume a low profile to facilitate insertion into a body lumen (not shown). For example, as best seen in FIG. 2A, the sheath 20 may be folded, twisted, wrapped, or otherwise compressed around or adjacent to the stiffening member 12 (e.g., using an internal vacuum with the lumen 26 of the sheath 20 and/or an external force). In the enlarged condition, the sheath 20 may unfold, untwist, unwrap, or otherwise expand to at least partially define the lumen 26, e.g., for receiving a fluid (e.g., a medicament, anti-thrombotic agent, and the like) and/or one or more instruments therethrough (not shown).

Because the sheath 20 is relatively thin-walled, the apparatus 10 may attain a relatively low profile when the sheath 20 is in its contracted condition, e.g., between about 0.1 and about ten millimeters (0.1-10 mm), and preferably between about 0.2 and about three millimeters (0.2-3 mm). Conversely, a relatively large lumen 26 may be provided when the sheath 20 is expanded to the enlarged condition, e.g., having a diameter or other maximum cross-section between about 0.3 and about one hundred millimeters (0.3-100 mm), and preferably between about 0.3 and about twenty millimeters (0.3-20 mm).

The sheath 20 may be formed from relatively thin, flexible material, as compared to the stiffening member 12. Thus, the sheath 20 may be flimsy, i.e., may have little or no rigidity such that the sheath 20 provides little resistance to expansion and/or contraction, and/or may conform substantially to anatomy within which it is deployed. As used herein, "flimsy" means that the material of the sheath 20 is not biased to assume any particular configuration or shape, and therefore, the sheath 20 may adopt whatever shape and/or configuration that is imposed upon it, e.g., by being folded or otherwise compressed, by being subjected to internal pressure or force, and the like. To achieve this, the sheath 20 may have a relatively thin wall thickness, e.g., between about 0.001-1.25 millimeters, and preferably between about 0.005-0.06 millimeter.

The sheath 20 may be constructed of materials that may be fabricated to a relatively thin, flexible configuration, e.g., polytetrafluoroethylene (PTFE), expanded polytetrafluoroethylene (EPTFE), fluorinated ethylenepropylene (FEP), polyethylene teraphathalate (PET), urethane, olefins, polyethylene (PE), silicone, latex, isoprene, chronoprene; and the like. The sheath 20 may be formed from a lubricious material and/or hydrophilically coated with a liquid silicone or other coating, e.g., for facilitating inserting one or more instruments (not shown) through the lumen 26. Preferably, the sheath 20 is formed from substantially inelastic material, i.e., such that a primary contribution to the sheath 20 expanding and contracting is unfolding or folding the material of the sheath 20. Thus, a total peripheral length of the sheath 20 may not change substantially between the contracted and enlarged conditions. Alternatively, the sheath 20 may be formed from an elastic material such that a secondary contribution to the sheath 20 expanding and contracting is an elasticity of the material of the sheath 20, i.e., such that the peripheral length of the sheath 20 may increase as the sheath 20 expands towards the enlarged condition.

The sheath 20 may be substantially nonporous. Alternatively, the sheath 20 may be porous, for example, substantially continuously along its length or at one or more locations, e.g., to allow fluid delivered into the lumen 26 to pass through the wall of the sheath 20 in a desired manner, e.g., to deliver fluid to a wall of a vessel (not shown) through which the sheath 20 extends. In a further alternative, the sheath 20 may include one or more discrete openings (not shown) at one or more locations along its length.

In addition or alternatively, the sheath 20 may include a thin-walled metal foil. Alternatively, the sheath 20 may include a thin mesh, e.g. a perforated urethane film and the like. In a further alternative, the lubricity of the sheath 20 may be enhanced by providing a lubricious coating, lining, ribbing, and the like (not shown), and/or applying a lubricant, e.g., to the interior surface of the sheath 20. The sheath 20 may include a single layer or multiple layers of such materials, such that a desired flexibility and lubricity is achieved. Thus, the sheath 20 may easily expand and/or line a body lumen to reduce friction and/or accommodate instruments being advanced through the body lumen, as explained further below.

Optionally, the sheath 20 may include one or more reinforcing elements (not shown). For example, a wire, thread, filament, and the like, formed from plastic, glass, composite, and/or metal, may be attached to an outer surface, an inner surface, and/or embedded in a wall of the sheath 20. In addition or alternatively, the sheath 20 may include relatively thickened regions that may be formed directly from the wall material. The reinforcing element(s) may extend circumferentially and/or helically around the sheath 20, and/or may extend axially along the sheath 20, depending upon the reinforcement desired. The reinforcement element(s) may also bias the sheath 20 assume a desired shape or configuration when expanded towards the enlarged condition.

In alternative embodiments, the sheath may be a tubular structure or a partially tubular structure of braided material (not shown) that may be attached to a stiffening member to provide a sheath apparatus. For example, the sheath may be formed from one or more plastic and/or metal wires, threads, or other strands that are braided, woven, and/or knit into a tubular body or into a sheet whose edges may be attached to a stiffening member, similar to the embodiments described elsewhere herein. The braided strands may be compressed to the contracted condition by twisting, folding, crimping, and/or wrapping, as described above, and/or by axial translation, e.g., pulling opposite ends of the sheath away from one another to cause the braided strand(s) to compress radially under the axial tension.

The proximal end 22 of the sheath 20 may include an annular collar or handle that may facilitate manipulating the sheath 20 and/or inserting one or more instruments into the lumen 26. In addition or alternatively, the proximal end 22 may include a hemostatic valve (also not shown) that may substantially seal the lumen 26 from proximal flow of fluid, yet may allow instruments to be introduced into the lumen 26, as is known in the art. For example, as shown in FIGS. 1A and 1B, a toughy borst valve 23 may be provided on the proximal end 22 of the sheath 20, e.g., to control passage into the lumen 26. Alternatively, other structures may be provided, e.g., a slit valve adapter, a removable clamp, an o-ring, a side port, an adjustable fixation device, and the like (not shown), for selectively sealing the lumen 26, manipulating the sheath 20, and/or for facilitating introducing instruments into the sheath 20.

The distal end 24 of the sheath 20 may include a variety of configurations. For example, as shown in FIGS. 1A and 2A, the distal end 24 of the sheath 20 may be offset proximally from the distal tip 17 of the stiffening member 12. In addition, the distal end 24 may include a rounded shape (e.g., as shown in FIG. 2A), a beveled shape (e.g., as shown in FIG. 6), or other tapered shapes that may enhance atraumatic advancement of the apparatus 10.

For example, as shown in FIG. 6, the taper 28" of the distal end 24" of the sheath 20" may facilitate tracking the apparatus 10" over a guide wire (not shown) and/or may facilitate advancing the apparatus 10" through a body lumen (also not shown). The taper 28" may minimize risk of the sheath 20" catching and/or may cause the sheath 20" to collapse towards the contracted condition as the apparatus 10" is advanced through a body lumen without needing external constraint. Alternatively, the distal end of the sheath may be substantially blunt (not shown).

The distal end 24 of the sheath 20 may be substantially closed or may include one or more openings. For example, as shown in FIG. 2A, the distal end 24 of the sheath 20 may be attached to the distal end 16 of the stiffening member 12 to substantially close the lumen 26 at the distal end 24. The distal end 24 of the sheath 20 may be detachable from the stiffening member 12 to release the sheath 20 from the stiffening member 12.

For example, the distal end 24 of the sheath 20 may be attached to the stiffening member 12 by an adhesive, solder, or other bonding materials, yet may be torn free or otherwise separated from the distal end 16 of the stiffening member 12, e.g., by pulling the sheath 20 proximally relative to the stiffening member 12 or by pushing the stiffening member 12 distally relative to the sheath 20. Alternatively, an instrument (not shown) may be advanced through the expandable member 20 and pushed against the closed distal end 24 to cause the distal end 24 to separate from the stiffening member 12. This may create an opening (not shown) in the distal end 24 of the sheath 20 through which fluid and/or one or more instruments (also not shown) may be advanced.

Alternatively, a mechanical connector (not shown) may be provided that may secure the distal ends 16, 24 together, and that may be actuated to release the distal end 24 of the sheath 20 from the distal end 16 of the stiffening member 12. In further alternatives, a cinch loop (not shown) may be provided on the distal end 24 that may be selectively opened or closed, or a removable clip (also not shown) may be provided. In addition or alternatively, the distal end 24 of the sheath 20 may be bonded to the distal end 16 of the stiffening member 12, e.g., using a bioabsorbable adhesive or other material that may dissolve when exposed to bodily fluids to provide an opening (not shown).

In a further alternative, shown in FIG. 5, the distal end 24' of the sheath 20' may include a break-away or penetrable region, e.g., a relatively thin or otherwise weakened region 30' of the sidewall of the sheath 20.' The weakened region 30' may tear along a weakened seam or may be punctured (not shown) when an instrument (also not shown) within the lumen 26' is pushed against the weakened region 30' to create an opening, thereby allowing the instrument to be advanced through the opening into the body lumen.

In yet another alternative, shown in FIG. 6, the distal end 24" of the sheath 20" may include one or more openings 28" communicating with the lumen 26," e.g., an axial opening defined by the tapered distal end 24," such that an instrument (not shown) inserted through the lumen 26" may be advanced from the opening 28" and into the body lumen.

Optionally, as shown in FIGS. 21A-21F, a sheath apparatus 610 may include a distal protection device, e.g., a balloon, or other expandable member 680, a filter (not shown, see FIG. 24 and description below), and the like, in addition to a stiffening member 612 and an expandable sheath 620. The balloon 680 may be disposed on a distal portion 616 of the stiffening member 612, e.g., adjacent to its distal tip 617. At least one lumen (not shown) within the stiffening member 612 may communicate with an interior of the balloon 680 for delivering inflation medium into and/or aspirating inflation medium from the interior for expanding and/or collapsing the balloon 680, as is known to those skilled in the art.

The balloon 680 may be used to anchor the apparatus 610 once positioned within a desired body lumen 690. In addition or alternatively, the balloon 680 may be used to substantially seal the body lumen 690, e.g., to prevent embolic material (not shown) released during a procedure from traveling downstream, and/or to facilitate isolated infusion, perfusion, agitation, or aspiration distal and/or proximal to the balloon, as explained further below. For example, as shown in FIGS. 22A-22C, the stiffening member 712 may include a lumen (not shown) therein with one or more ports 719 located distally relative to an occlusion balloon 780. In yet another alternative, as shown in FIG. 23, ports 719' may be provided that are located proximally relative to an occlusion balloon 780.'

Figure 24:
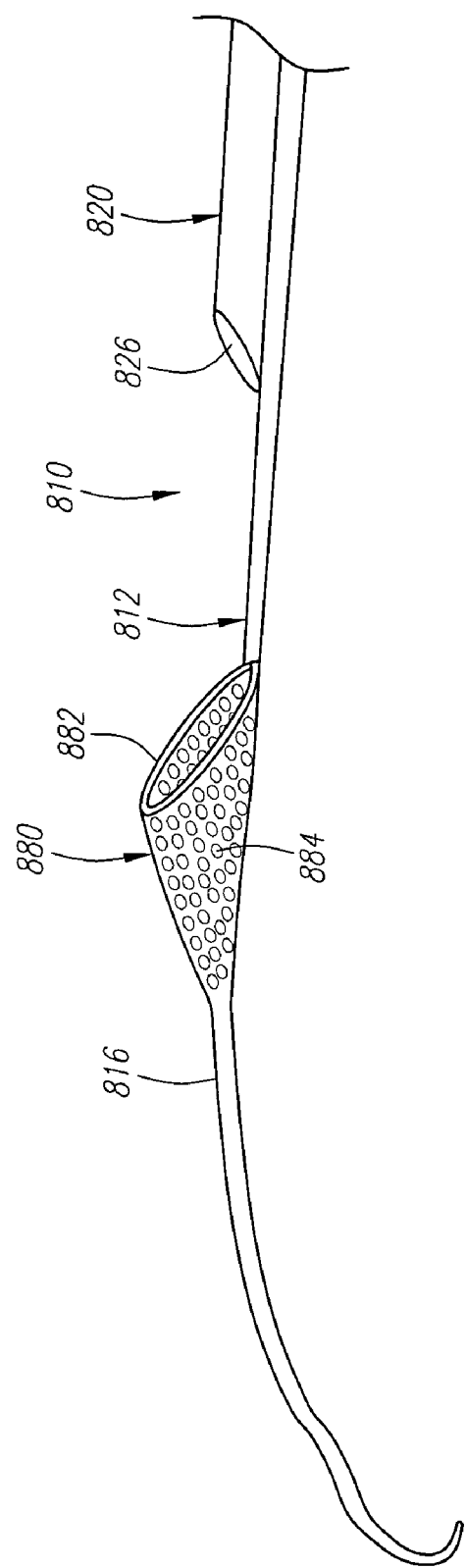
FIG. 24 is a perspective view of a distal end of another embodiment of a sheath apparatus including a filter attached to a stiffening member extending from the sheath.

Alternatively, as shown in FIG. 24, a filter 880 may be provided on any of a stiffening member 812 of a sheath apparatus 810. Preferably, the filter is attached to a distal end 816 of the stiffening member 812 distal to a sheath 820. The stiffening member 812 and sheath 820 may be any of the embodiments described herein. The filter 880 may include an expandable frame 882 and a mesh or porous member 884 attached to the frame 882.

The frame 882 may be biased to expand away from the stiffening member 812, e.g., to define a hoop that may expand the mesh 884 across a blood vessel or other body lumen (not shown). In addition or alternatively, the frame 882 may include one or more struts, e.g., a plurality of struts (not shown) that may extend generally radially away from the stiffening member 812. The frame 882 may be formed from an elastic or superelastic material, e.g., Nitinol, or may be selectively expandable and/or collapsible, e.g., including one or more lumens (not shown) into which fluid may be delivered to expand the frame 882.

The mesh 884 may include any material having a appropriate pore size for collecting emboli or other particles larger than a predetermined size. The mesh 884 and frame 882 may be disposed such that the mesh 884 opens towards the sheath 820, although alternatively, the mesh 884 may open away from the sheath 820 (not shown).

The filter 880 may be deployed similar to the balloon 780 described above to capture emboli released during a procedure. For example, the filter 880 may be deployed from a sheath or catheter (not shown) overlying the apparatus 810 and/or may be captured within a sheath or catheter upon completing a procedure during which emboli may be collected within the filter 880. Alternatively, a filament or other control element may be provided that may be actuated from a proximal end (not shown) of the apparatus 810 for selectively collapsing the filter 880 to retain emboli captured therein.

In a further alternative, as shown in FIG. 7, the distal end 424 of the sheath 420 may include an expandable cuff 430. The cuff 430 may be an inflatable annular balloon attached around a periphery of the sheath 420. One or more lumens (not shown) may be provided within the stiffening member 412 that communicate with the interior of the cuff 430 to expand and/or collapse the cuff 430. The expanded cuff 430 may be used to fix the sheath 420 within a body lumen (not shown) and/or may serve to isolate a distal segment of a body lumen from a segment proximal to the expanded cuff 430.

For example, the sheath 420 may be delivered into a blood vessel, and the cuff 430 may be expanded to seal the vessel. One or more intravascular manipulations or procedures may be performed within the vessel proximal to the expanded cuff 430. Thus, if embolic debris is released within the proximal portion of the vessel, the cuff 430 may prevent the debris from passing to the distal portion of the blood vessel.

In another alternative, the proximal opening 426 of the sheath 420 may be positioned within a blood vessel (not shown), thereby creating a bypass or shunt channel that may be positioned within a body lumen beginning at the proximal opening 426 and extending through the lumen 426 of the sheath 420 to the distal cuff 430.

In a further alternative, one or more lumens (not shown) may be created within or along a wall of the sheath 420 itself. Optionally, one or more cuffs or pockets (not shown) may be provided at one or more locations along the sheath 420, e.g., to anchor the sheath 420, to restrict flow, e.g., for the purpose of retrograde infusion of contrast, and/or to bias the sheath 420 to expand to a particular shape or configuration.

Returning to FIGS. 1A-2B, in one embodiment, the sheath 20 may be a substantially enclosed tubular body that is attached to the stiffening member 12 at one or more locations between the proximal and distal ends of the stiffening member 12. For example, the sheath 20 may be attached to the stiffening member 12 only at the distal ends 24, 16. Alternatively, the sheath 20 may be attached to the stiffening member 12 at or near the proximal end 22, the distal end 24 of the sheath 20, or both, e.g., when the stiffening member 12 is disposed along a wall of the sheath 20.

Optionally, the sheath 20 may be attached to the stiffening member 12 intermittently, e.g., at one or more additional locations between the proximal and distal ends 22, 24. Alternatively, the stiffening member 12 may be attached substantially continuously to the sheath 20 between the proximal and distal ends 22, 24 of the sheath 20. The stiffening member 12 may be attached to an interior of the sheath 20, i.e., within the lumen 26, or, alternatively, may be attached to an exterior of the sheath 20. The sheath 20 and the stiffening member 12 may be attached to one another using any known method, e.g., bonding with adhesive, sonic welding, sutures or other strands (not shown) and the like.

Alternatively, the stiffening member 12 may be received in a separate pocket or lumen (not shown) of the sheath 20 that extends between the proximal and distal ends 22, 24 of the sheath 20. The stiffening member 12 may be loose within the pocket or lumen or may be attached to the sheath 20 within the lumen, as described above.

In another embodiment, shown in FIGS. 4A and 4B, the sheath 120 may be a sheet of material whose edges 121 are attached to a stiffening member 112. Thus, the stiffening member 12 may partially define the lumen 126, along with the sheet of the sheath 120. The sheath 120 may be attached substantially continuously along the length of the stiffening member 112, although, alternatively, the sheath 120 may be attached intermittently to the stiffening member 112, as described previously.

Optionally, any of the sheaths described above, e.g., the sheath 20 shown in FIGS. 1A-2B may be configured to split, e.g., along one or more seams (not shown) extending at least partially from the proximal end 22 towards the distal end 24, and/or to separate from the stiffening member 12. For example, the sheath 20 may include two or more sets of intermittent perforations and/or relatively thin-walled seams (not shown) that extend between the proximal and distal ends 22, 24. In addition or alternatively, the material of the sheath 20 may be biased to tear preferentially, e.g., along the longitudinal axis 18, to separate the sheath 20 into two or more longitudinal strips (not shown). These features may facilitate removing the sheath 20 and/or the entire apparatus 10 from a body lumen when an instrument (not shown) is disposed within the lumen 26, for example, when the instrument is intended to be substantially permanently implanted within the body lumen.

The apparatus 10 may also include a constraint for covering and/or protecting the sheath during advancement through a patient's vasculature or other body passages. For example, as shown in FIG. 8, one or more wires, threads, monofilaments, or other strands 50 may be disposed around the sheath 20 to maintain the sheath 20 in its contracted condition. The strands 50 may include a plurality of loops 52 that extend around the sheath 20 and are secured using one or more removable filaments (not shown) fed through the loops 52. To release the sheath 20, the removable filament(s) may be removed from the loops 52, e.g., by pulling the removable filament(s) from the proximal end of the apparatus 10. The loops 52 may then be released and their strand(s) may be removed.

Alternatively, other constraints, e.g., wraps, ties, adhesives, bio-absorbable encapsulating materials, e.g., sucrose, and the like, may be used (not shown). In further alternatives, a catheter, sheath, or other tubular member (also not shown) may be provided. For example, as shown in FIGS. 13A and 13B, a catheter 80 may be used that may include a lumen 82 within which the apparatus 10 (or any other sheath apparatus described herein) may be disposed when the sheath 20 is in the contracted condition. The apparatus 10 may include a pushing element 84, e.g., a wire or other elongate member extending from the stiffening member 12 (see FIGS. 1A-2B, not shown in FIGS. 13A and 13B). The pushing element 84 may be advanced distally relative to the catheter 80 to deploy the apparatus 10, as shown in FIG. 13B, or may be pulled proximally to retract the apparatus 10 into the catheter 80, as shown in FIG. 13A.

In another embodiment, shown in FIGS. 16A-17C, an outer sheath 180 may be provided that is at least partially bonded to a sheath apparatus 110 to maintain an expandable sheath 120 in a contracted condition. The outer sheath 180 may be formed from materials similar to the expandable sheath 120, e.g., having a wall thickness between about 0.005-0.06 millimeter (mm). Thus, the outer sheath 180 may be substantially flexible and/or conformable to facilitate advancing the apparatus 110 and outer sheath 180 through a body lumen of a patient.

The apparatus 110 may include a stiffening member 112, similar to that described above with reference to FIGS. 3A-4B, to which the expandable sheath 120 may also be attached, similar to other embodiments described above. The stiffening member 112 may include one or more lumens 119 (three exemplary lumens being shown), and the outer sheath 180 may be bonded or otherwise attached to the stiffening member 112, e.g., continuously or intermittently along a length of the stiffening member 112. The lumen(s) in the stiffening member 112 may provide infusion, aspiration, agitation, and/or perfusion through the apparatus 110, e.g., from the proximal end to the distal end of the apparatus 110. Alternatively, the outer sheath 180 may be attached directly to the expandable sheath 120, e.g., at a location around the periphery and/or along a length of the expandable sheath 120 (not shown).

Figure 17A:
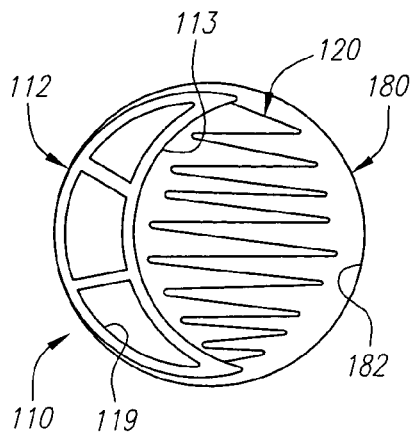
FIGS. 17A-17C are cross-sectional views of the apparatus shown in FIGS. 16A-16C, respectively.

As best seen in FIGS. 16A and 17A, the outer sheath 180 may at least partially define a lumen 182 (either alone or along with the stiffening member 112) within which the expandable sheath 120 may be received in its contracted condition. In addition, the outer sheath 180 may include one or more weakened regions 186, e.g., extending between proximal and distal ends (not shown) of the outer sheath 180. The weakened region(s) 186 may include intermittent perforations and/or continuous or intermittent thin-walled regions that may extend, e.g., substantially axially along the outer sheath 180.

The weakened region(s) 186 may separate upon exposure to internal pressure to allow the expandable sheath 120 to expand towards its enlarged condition. For example, fluid may be introduced into the lumen 182 of the outer sheath 180 until sufficient pressure develops to cause the weakened region(s) 186 to tear or otherwise separate. Alternatively, fluid or an instrument (not shown) may be introduced into the expandable sheath 120 such that the expandable sheath 120 expands until it pushes radially outwardly against the outer sheath 180 and causes the weakened region(s) 186 to separate.

Figure 16B:
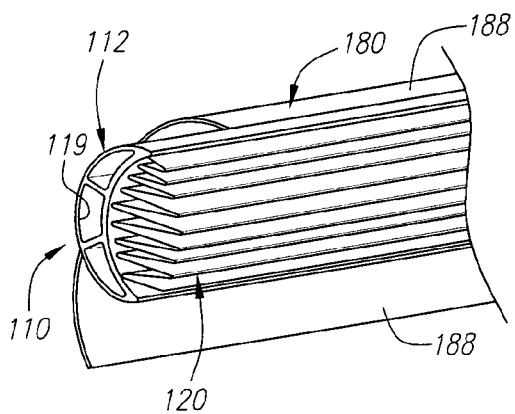
Figure 17B:
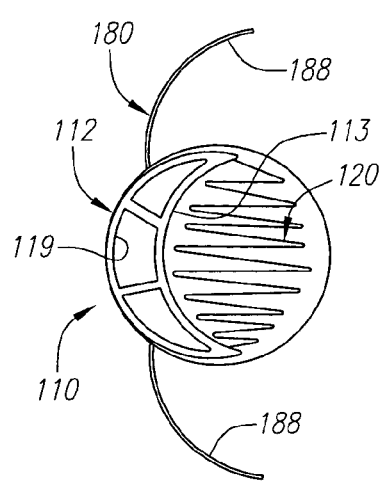
Figure 16C:
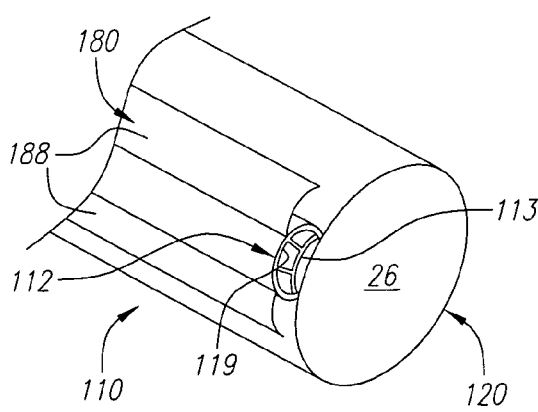
Figure 17C:
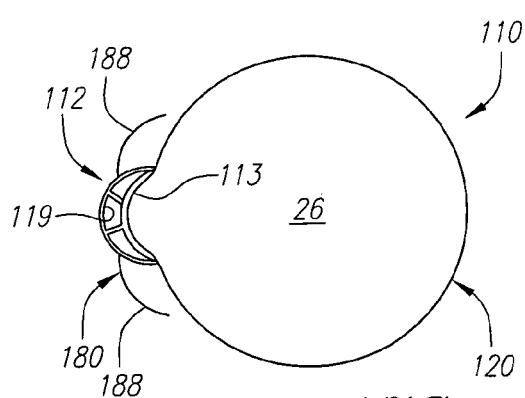

For example, during use, the apparatus 110 and outer sheath 180 may be advanced through a body lumen, e.g., a blood vessel and the like (not shown), with the outer sheath 180 intact and the expandable sheath 120 in its contracted condition, as shown in FIGS. 16A and 17A. Once a desired location is reached, internal pressure may be applied to separate the weakened region(s) 186 of the outer sheath 180, as shown in FIGS. 16B and 17B. The expandable sheath 120 may then be expanded to its enlarged condition, as shown in FIGS. 16C and 17C. The separated portions 188 of the outer sheath 180 may be substantially flexible such that they do not interfere substantially with the expansion of the expandable sheath 120 and/or may conform substantially to the shape of the expandable sheath 120 as it expands.

In a further alternative, with reference to FIGS. 1A-2B, when a constraint is provided around the sheath 20, the sheath 20 need not be attached to the stiffening member 12. The sheath 20, e.g., a tubular body, may simply be disposed around the stiffening member 12 and folded, twisted, crimped, wrapped, or otherwise compressed into the contracted condition around or adjacent to the stiffening member 12 before being inserted into or otherwise constrained by the constraint. In addition or alternatively, vacuum pressure, either alone or in conjunction with folding, may be used to compress the sheath 20 and/or fluid may be infused into the lumen 26 to expand the sheath 20, as explained further below.

Although only one stiffening member 12 is shown in FIGS. 1A-2B, it will be appreciated that a sheath apparatus in accordance with the present invention may include more than one stiffening member. For example, as shown in FIGS. 9A and 9B, an embodiment of a sheath apparatus 210 is shown that includes two stiffening members 212 to which an expandable membrane or other sheath 220 is attached. The sheath 220 may be compressed to a contracted condition, shown in FIG. 9A, e.g., by twisting the stiffening members 212 about longitudinal axis 218 to wind the sheath 220 around the stiffening members 212. The sheath 220 may be unwound and expanded to an enlarged condition, shown in FIG. 9B, by untwisting the stiffening members 212, thereby providing lumen 226 within the sheath 220.

Figure 10B:
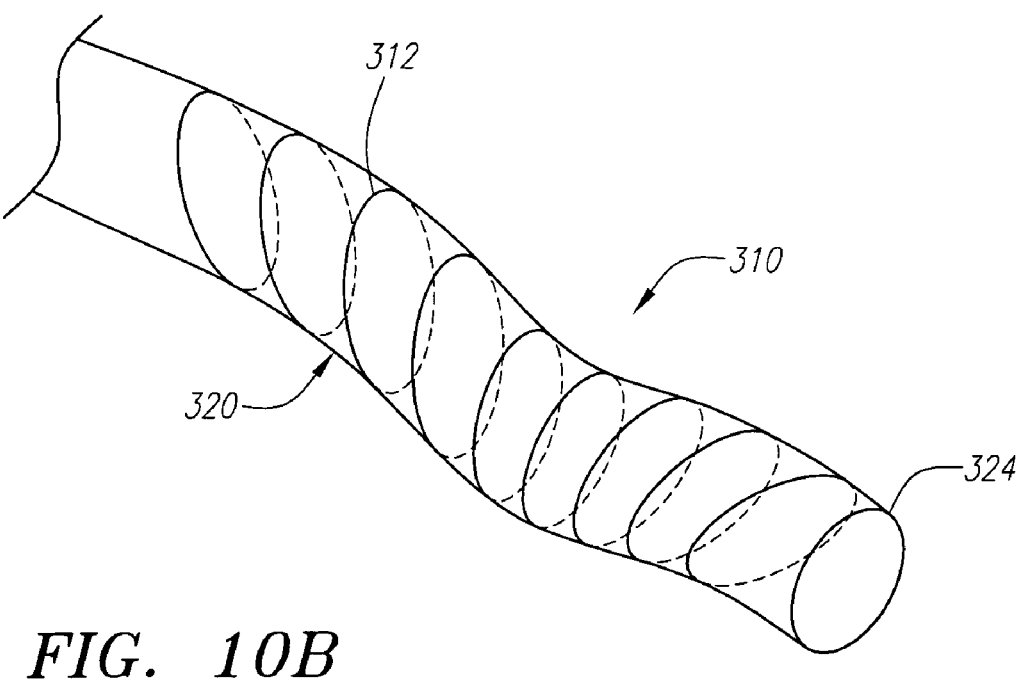

In addition, although the stiffening members 12, 212 shown in FIGS. 1A-2B, 9A, and 9B extend generally parallel to the longitudinal axis 18, 218, other stiffening members may also be provided in addition or instead of the stiffening member(s) 12, 212. For example, as shown in FIGS. 10A and 10B, one or more reinforcing members 312 may be provided that extend helically around a tubular sheath 320. The reinforcing members 312 may be wires or other strands attached to an outer or inner surface of the sheath 320 or embedded within a wall of the sheath 320. One or more helical reinforcing members may also facilitate expanding and/or collapsing the sheath 320. For example, ends of the reinforcing member(s) 312 may pulled axially away from one to compress the sheath 320. In addition or alternatively, the reinforcing member(s) 312 may be biased to expand, e.g., towards the configuration shown in FIG. 10B, to facilitate expanding the sheath 320 towards the enlarged condition.

In addition or alternatively, one or circumferential or peripheral rings or strands (not shown) may be provided around the sheath 320. Such reinforcing rings or strands may support the sheath 320 and/or bias the sheath 320 towards the enlarged condition, similar to the helical reinforcing member(s) described above.

Further, although the apparatus described above include an expandable sheath having a single lumen, it will be appreciated that it may be possible to provide one or more sheaths, each including one or more lumens therein. For example, a sheath may be fabricated to have multiple lumens, e.g. by extrusion. As a further example, a plurality of expandable sheaths, similar to those described above, may be attached to one another and/or to one or more common stiffening members to provide an apparatus with multiple expandable lumens (not shown). The sheaths may be concentric with one another, e.g., disposed loosely within one another, or attached along one or more edges to one another. Alternatively, the sheaths may be disposed adjacent to one another, e.g., attached together or to one or more common stiffening members. Thus, multiple instruments may be advanced through respective lumens of the sheaths in conjunction with one another.

Optionally, one or more of the components of the sheath apparatus described above, e.g., stiffening member(s), sheath, and/or constraint, may include one or more radiopaque markers, e.g., bands or other elements made from radiopaque material, radiopaque inks or other depositions, and the like (not shown). Such markers and/or radiopaque material may facilitate imaging and/or monitoring the apparatus during its use, e.g., using fluoroscopy. In addition, markers may be provided that are spaced relative to one another in a predetermined manner, e.g., at known distances from one another, to denote distances and/or facilitate mapping and/or accessing a patient's vasculature. Alternatively, other external or internal imaging systems and methods may be used, e.g., magnetic resonance imaging ("MRI"), ultrasound, and the like, as is well known in the art.

A sheath apparatus in accordance with the present invention may be used to provide access to a variety of body lumens, e.g., to perform a diagnostic and/or therapeutic procedure. Generally, the apparatus, with an expandable sheath in a contracted condition, may be introduced into an entry site, e.g., a natural or created opening in a patient's body, and advanced into one or more body passages, including created passages, e.g., dissection planes, within the patient's body. Preferably, the apparatus is advanced from the entry site until a distal end of the sheath is disposed within a target body lumen while a proximal end of the sheath remains outside the entry site. Because of its low profile, the apparatus may be easily advanced through tortuous anatomy until the distal end is disposed within relatively small, difficult to access body lumens.

The sheath may then be expanded to an enlarged condition, thereby defining a lumen within the sheath. Thus, the lumen defined by the sheath may extend from the entry site through any intervening body passages to the target body lumen or site to provide a path from the entry site to the target body lumen or site. Optionally, if, as described above, the sheath is maintained and/or covered in the contracted condition by a constraint, the constraint may be at least partially removed from the sheath before the sheath is expanded to the enlarged condition.

A diagnostic and/or therapeutic procedure, such as the exemplary procedures described below, may be performed within the body lumen via the lumen defined by the sheath. Upon completing the procedure(s), the sheath may be withdrawn from the body lumen, and preferably from the patient's body.

For example, as shown in FIGS. 11A-11F, a sheath apparatus 10 may be used to facilitate delivering a stent 60 within a stenosis or occlusion 92 within a blood vessel 90. The vessel 90 may be an artery or vein within a coronary, carotid, cerebral, or other vessel, e.g., within a patient's coronary, peripheral, or neuro vasculature.

Figure 11A:
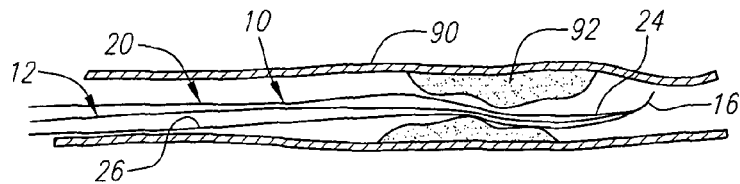
FIGS. 11A-11F are partial cross-sections of a patient's vasculature, showing a method for delivering a stent across a stenosis using a sheath apparatus, in accordance with the present invention.

As shown in FIG. 11A, the apparatus 10, with the sheath 20 in its contracted condition, may be advanced from a percutaneous entry site (not shown) and introduced into the patient's vasculature, until the distal end 16 is disposed within the target vessel 90. For example, a guidewire (not shown) may be previously placed from the percutaneous entry site to the vessel 90 beyond the stenosis 92 using conventional methods. The apparatus 10 may be advanced over the guidewire until the distal end 24 of the sheath 20 is positioned within or beyond the stenosis 92, as shown in FIG. 11A. If the apparatus 10 includes a stiffening member 12, the stiffening member 12 may include a guidewire lumen (not shown) such that the guidewire may be inserted through the guidewire lumen to advance the apparatus 10 over the guidewire. Alternatively, the sheath 20, in its contracted condition may be advanced without a previously placed guidewire. The distal tip of the sheath 20 or stiffening member 12 may facilitate navigation through the vasculature, e.g., by being substantially flexible or floppy, to avoid trauma to the vasculature during advancement, or by being shaped, shapeable, or deformable to enable steering during advancement.

Once the apparatus 10 is positioned within the vessel 90, any constraint (not shown) maintaining the sheath 20 in the contracted condition or otherwise covering the sheath 20 may be removed, e.g., mechanically, chemically (e.g., bio-absorbable sutures), and/or physiologically (e.g., heat-activated nitinol ties). For example, as described above, this may involve retracting an overlying catheter or sheath (not shown), or removing loops or other strands (also not shown) surrounding the sheath 20.

The sheath 20 may then be expanded from its contracted condition to its enlarged condition. For example, a fluid (not shown) may be introduced into the lumen 26 to expand the sheath 20, e.g., such that the sheath 20 expands to line or otherwise contact walls of one or more vessels within the patient's vasculature, e.g., between the entry site and the vessel 90. Alternatively, the sheath 20 may simply be released such that the sheath 20 is free to expand as one or more instruments, such as the catheter 62 and stent 60, are advanced through the lumen 26, as shown in FIG. 11B.

Figure 11B:
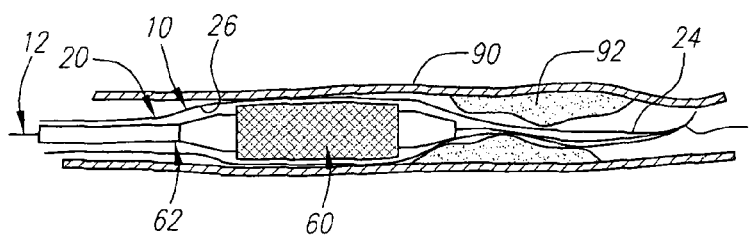

With continued reference to FIG. 11B, one or more instruments may be introduced through the lumen 26 defined by the sheath 20 into the vessel 90. For example, a catheter 62 carrying the stent 60 may be introduced into the proximal end 22 (not shown in FIGS. 1A-11F) of the sheath 20 and advanced through the lumen 26 until the stent 60 is located within the vessel 90. The stent 60 may be any known endoprosthesis, e.g., a balloon-expandable or self-expanding stent, and the catheter 62 may include any known delivery apparatus, e.g., including a balloon, sheath, nose cone, and/or other elements. Optionally, other instruments, e.g., thrombectomy devices, agitation devices, balloon catheters, filters, occlusion devices, and the like (not shown) may be introduced through the sheath 20 before or after the catheter 62, e.g., to dilate the stenosis 92 and/or to provide distal protection, i.e., capture embolic material released during the procedure.

The guidewire or other rail over which the apparatus 10 may be advanced may be removed before any instrument(s) are advanced through the sheath 20, or the guidewire may remain in place across the stenosis 92. In addition, if the apparatus 10 includes a concentric stiffening member 12 within the sheath 20, the catheter 62 may be advanced over the stiffening member 12, i.e., between the stiffening member 12 and the sheath 20, as shown in FIG. 11B. Alternatively, the stiffening member 12 may be removed from the sheath 20 if the sheath is detachable from the stiffening member 12 (not shown). In a further alternative, such as that shown in FIGS. 4A and 4B, the instrument(s) (not shown in FIGS. 4A and 4B) may be advanced through the lumen 126 adjacent to the stiffening member 12. Thus, one advantage of delivering a catheter or other instrument within the sheath 20 is that there may be no need for a guidewire lumen in the instrument, which may allow the profile of the instrument to be reduced as compared to instruments that are delivered over a guidewire.

Figure 11C:
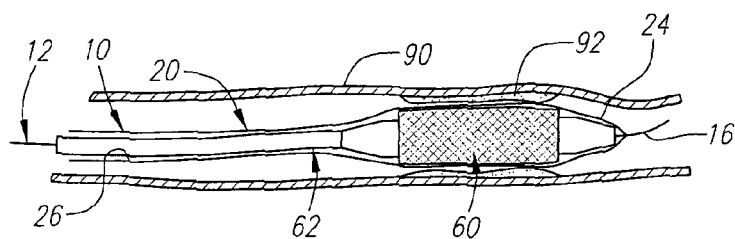

With continued reference to FIG. 1B, the lubricious nature of the sheath 20 may facilitate advancing the catheter 62 through the lumen 26, and, consequently, through any narrow, tortuous, diseased, and/or friable regions of the patient's vasculature. For example, the sheath 20 may translate axial forces, e.g., created when an instrument, such as the catheter 62, is pushed against or into a narrow region, into radial forces that may facilitate dilating the narrow region to accommodate the instrument passing therethrough. This action may be enhanced further by pressurizing the sheath 20 internally, e.g., by introducing a fluid into the lumen 26. Thus, the sheath 20 may facilitate advancing the stent 60 across the stenosis 92, as shown in FIG. 11C.

In addition, the sheath 20 may substantially reduce the risk of perforating or otherwise damaging the walls of vessels within the vasculature and/or snagging an instrument, since the sheath 20 may guide any instruments advanced through the sheath 20 along the lubricious path of the lumen 26. Further, the sheath 20 may minimize the risk of embolic material and the like from being dislodged from the patient's vasculature, since the sheath 20 may expand to line the walls, thereby restraining plaque, thrombus, and the like between the sheath 20 and the vessels' walls.

Figure 11D:
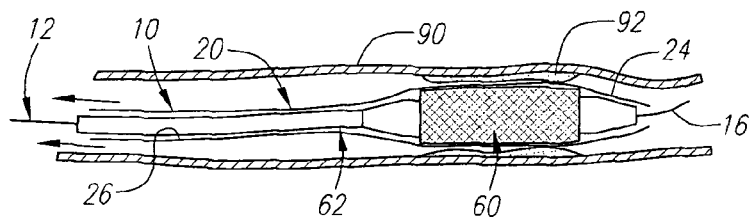

If the distal end 24 of the sheath 20 is closed, an opening 28 may be created to accommodate advancing one or more instruments through the lumen 26 and out of the sheath 20. For example, as explained above, the distal end 24 may be separated from the stiffening member 12 when the first instrument, e.g., the catheter 62 carrying the stent 60 is advanced through the lumen 26 and against the distal end 24, as shown in FIG. 11D. Alternatively, if the distal end 24 of the sheath 20 is attached to a stiffening member 12, the distal end 24 may be separated from the stiffening member 12, e.g., by advancing the stiffening member 12 distally and/or retracting the sheath 20 proximally, to create the opening 28, e.g., before or after introducing the catheter 62 or other instrument (not shown) into the lumen 26.

In a further alternative, as shown in FIG. 5 and described above, the sheath 20' may include a weakened region 30' in the distal end 24' that may be used to create an opening (not shown in FIG. 5). For example, a fluid, e.g., saline and/or contrast, may be introduced into the lumen 26' of the sheath 20' until sufficient internal pressure is created to cause the weakened region 30' to rupture or tear. Alternatively, an instrument (e.g., the catheter 62 shown in FIGS. 11B-11F, a guidewire, and the like, not shown), may be advanced into the lumen 26' and pushed against the weakened region 30' to cause the weakened region 30' to fail and create an opening. In still a further alternative, an apparatus 10," such as that shown in FIG. 6, may be used that includes a sheath 20" with an opening 28" already provided in the distal end 24."

Figure 11E:
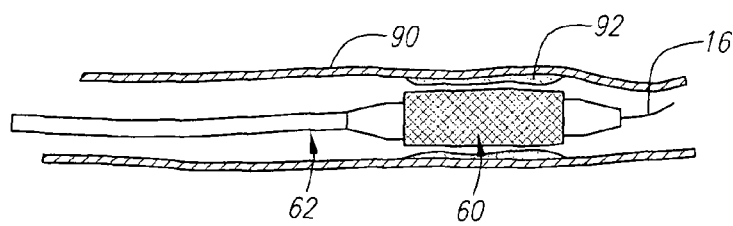
Figure 11F:
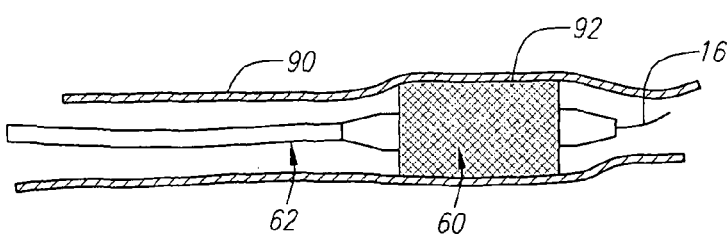

Turning to FIG. 11E, once the stent 60 is positioned across the stenosis 92, the sheath 20 may be at least partially retracted to expose the stent 60 and/or the catheter 62 within the vessel 90 and/or stenosis 92. The stent 60 may be expanded, as shown in FIG. 11F, e.g., using conventional methods to dilate and/or scaffold the stenosis 92. Once the stent 60 is delivered (and any additional procedures completed), the catheter 62 and the apparatus 10 may be removed from the vessel 90, and the patient's vasculature via the entry site.

In one embodiment, the catheter 62 or other instruments (not shown) may first be removed into and through the sheath 20, whereupon the sheath 20 may be removed. If desired, the sheath 20 may be collapsed at least partially from the enlarged condition before removing the sheath 20 from the vessel 90 by aspirating any fluid from within the lumen 26 of the sheath 20, e.g., by connecting a source of vacuum to the proximal end 22 of the sheath 20. Alternatively, a catheter or other tubular member (not shown) may be advanced over the sheath 20 to facilitate its removal. In another alternative, the sheath 20 may be removed simultaneously with the catheter 62 or other instrument(s), e.g., by retracting the instrument(s) into the sheath 20. In yet another alternative, the sheath 20 may be removed from the patient before the catheter 62 or other instrument(s) are removed. It will be appreciated that external imaging, e.g., fluoroscopy, MRI, and/or ultrasound, may be used to monitor the procedure, and that any of the components, e.g., the apparatus 10, the stent 60, and/or the catheter 62 may include elements, e.g., radiopaque markers (not shown) for facilitating such imaging during their advancement and/or removal.

Figure 21A:
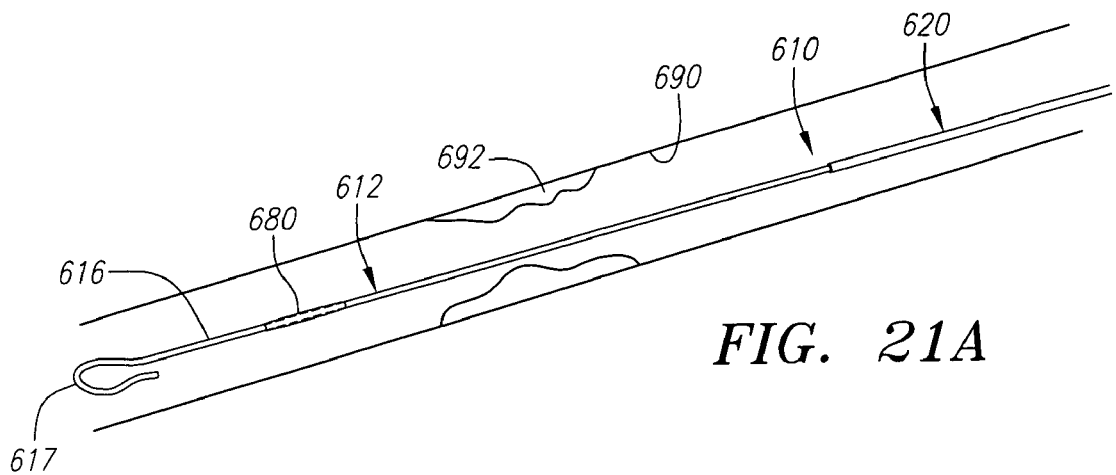
FIGS. 21A-21F are cross-sectional views of a blood vessel, showing a method for treating a stenosis therein, in accordance with the present invention.

In a further alternative, shown in FIGS. 21A-21F, a distal protection device, e.g., balloon 680, may be provided on a sheath apparatus 610, which may be similar to any of the embodiments described above. Initially, as shown in FIG. 21A, the balloon 680 and an expandable sheath 620 of the apparatus 610 may be provided collapsed, and the apparatus 610 may be advanced into a body lumen 690, e.g., an artery or other blood vessel having a stenosis 692 therein via a percutaneous entry site (not shown). Preferably, a distal end 616 of a stiffening member 612 of the apparatus 610 is advanced through the stenosis 692 until the balloon 680 is located downstream or distal to the stenosis 692. The apparatus 610 may include a constraint (not shown) for covering the balloon 680 and/or for maintaining the sheath 620 in the contracted condition, as described previously.

Figure 21B:
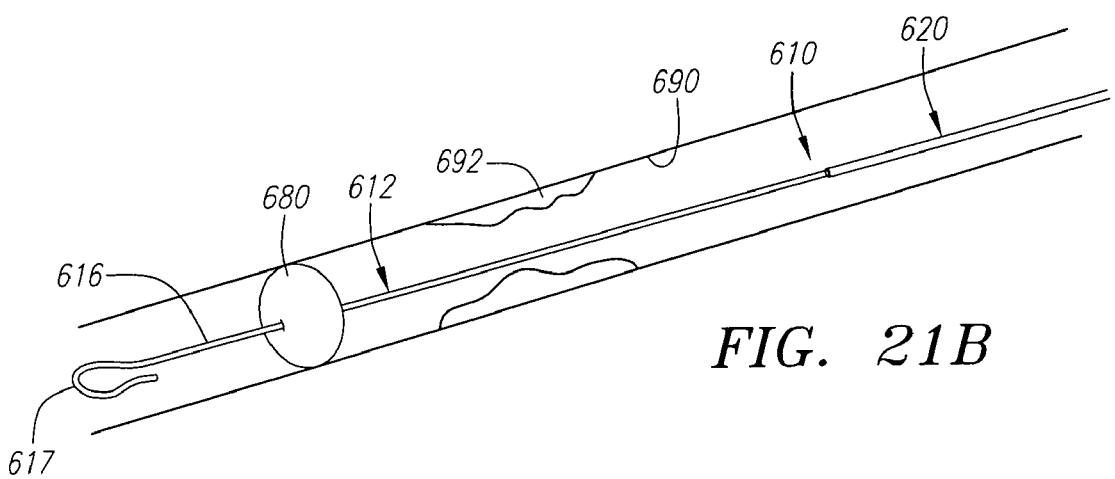

Once the apparatus 610 is positioned as desired, the balloon 680 may be expanded, as shown in FIG. 21B, to substantially seal the lumen 690. Thus, the balloon 680 may prevent blood or other fluid from flowing downstream from the lumen 690, thereby allowing fluids to be delivered into the proximity of the stenosis 692 and/or preventing embolic material released during the procedure from being carried downstream from the stenosis 692.

Figure 21C:
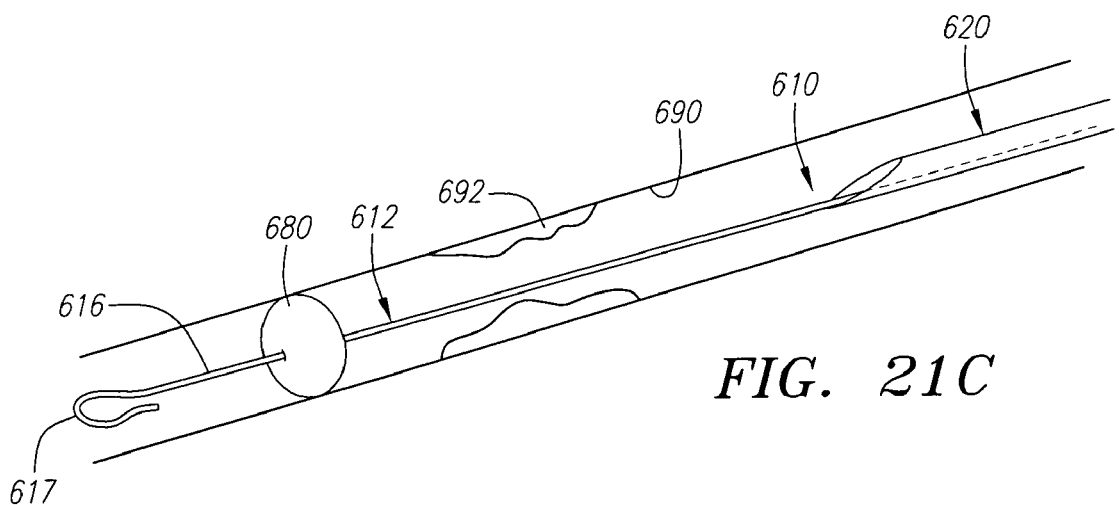

As shown in FIG. 21C, the sheath 620 may be expanded to its enlarged condition, e.g., by introducing fluid and/or instrument(s) into its lumen 626. If the sheath 620 is maintained in the contracted condition using a constraint (not shown), the constraint may be removed, as described above, before the sheath 620 is expanded.

Figure 21D:
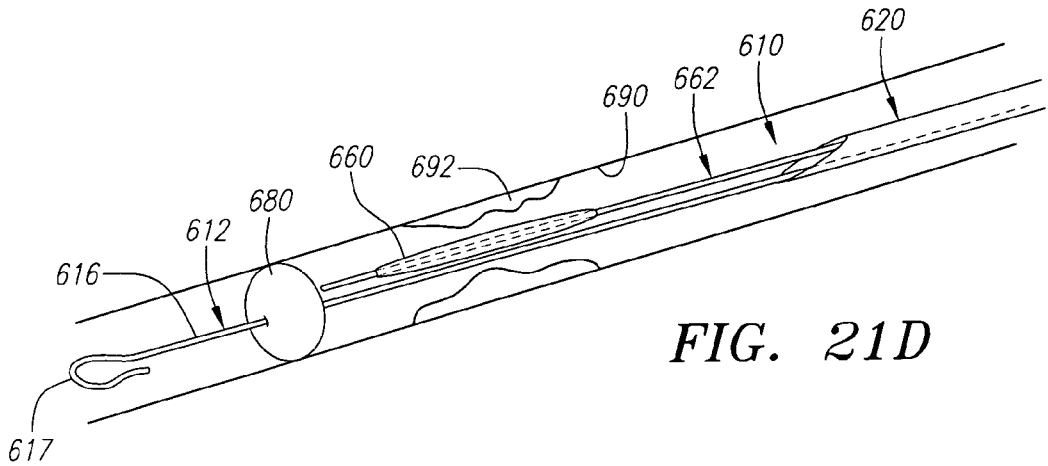
Figure 21E:
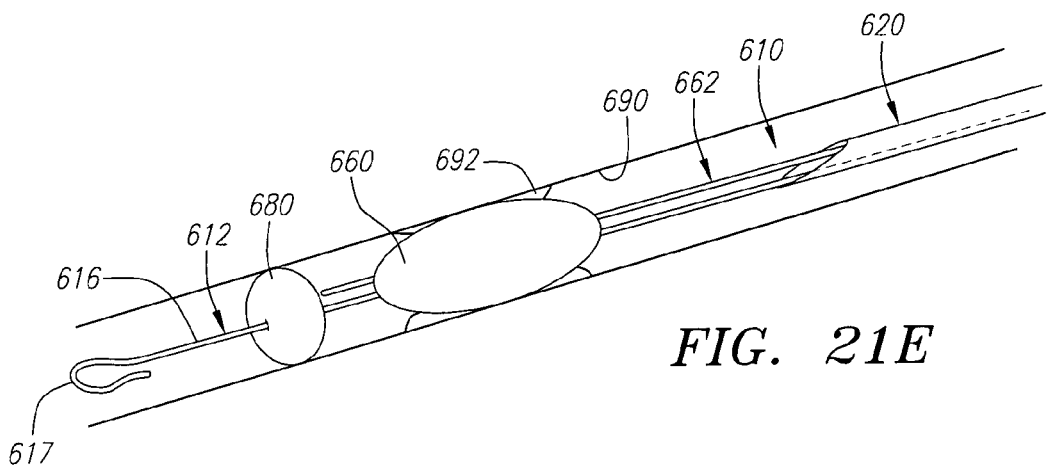

One or more instruments may then be advanced into the lumen 690 via the sheath 620. For example, as shown in FIG. 21D, an angioplasty balloon catheter 662 may be advanced through the lumen 626 of the sheath 620 until a balloon 660 thereon is disposed within the stenosis 692, as shown in FIG. 21D. The balloon 660 may then be expanded to dilate the stenosis 692, as is well known to those skilled in the art. After the stenosis 692 is sufficiently dilated, the balloon 660 may be collapsed, and the catheter 662 may be withdrawn through the sheath 620. If desired, other instruments, e.g., balloon catheters, stents, and the like (not shown) may be advanced through the sheath 620 to treat the stenosis 692.

Figure 21F:
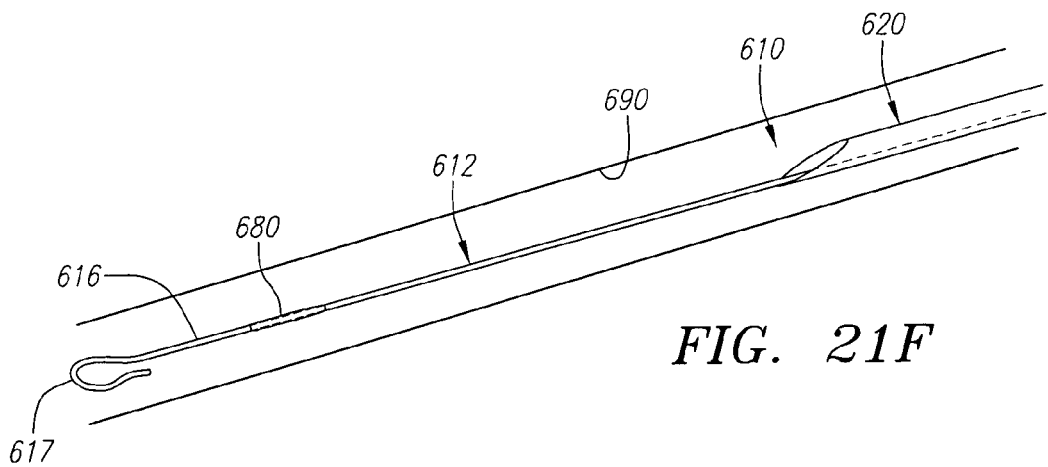

Once the stenosis 692 is treated, any embolic material (not shown) released during the procedure and/or disposed adjacent the balloon 680 may be removed. For example, a catheter (not shown) may be advanced through the sheath 620 or over the device 610 until its distal end is located adjacent the balloon 680. A source of vacuum (also not shown) may be coupled to the catheter to aspirate embolic material and/or fluid from the lumen 690 adjacent to the balloon 680, as is well known to those skilled in the art. Alternatively, an aspiration lumen (not shown) may be provided in the stiffening member 612 that may be used to aspirate material from the lumen 690. As shown in FIG. 21F, the balloon 680 may then be collapsed, and the apparatus 610 may then be removed from the lumen 690.

In yet another alternative, turning to FIGS. 22A-22C, an apparatus 710 is shown that includes a stiffening member 712, an expandable sheath 720, and an occlusion balloon 780, similar to the embodiment shown in FIGS. 21A-21F. In addition, the apparatus 710 may be used to deliver fluid into a lumen 790, e.g., distal to the balloon 780. Specifically, the stiffening member 712 may include a lumen (not shown) that extends between its proximal end (not shown) and its distal end 716. The stiffening member 712 may include one or more ports 719 located distal to the balloon 780 that communicate with the lumen, such that fluid infused through the lumen may be delivered into the body lumen 790 distal to the balloon 780, as shown in FIG. 22B. Alternatively, as shown in FIG. 23, one or more ports 719' may be provided in the stiffening member 712' proximal to the balloon 780' for delivering fluid proximal to the balloon 780.'

Thus, during a procedure, such as the stent delivery or angioplasty procedures described above, the apparatus 710 may be delivered into a body lumen 790 with the sheath 720 in its contracted condition, as shown in FIG. 22A. The balloon 780 may be expanded to substantially seal the lumen 790, and then fluid may be delivered via the port(s) 719 into the lumen 790 upstream from the balloon 780, e.g., to provide retrograde perfusion into the body lumen 790.

In a further alternative, a filter or other distal protection element may be provided, such as the filter 880 shown in FIG. 24 and described above. Similar to the balloon 780, the filter 880 may capture embolic material released during a procedure, such as those described elsewhere herein.

Figure 12A:
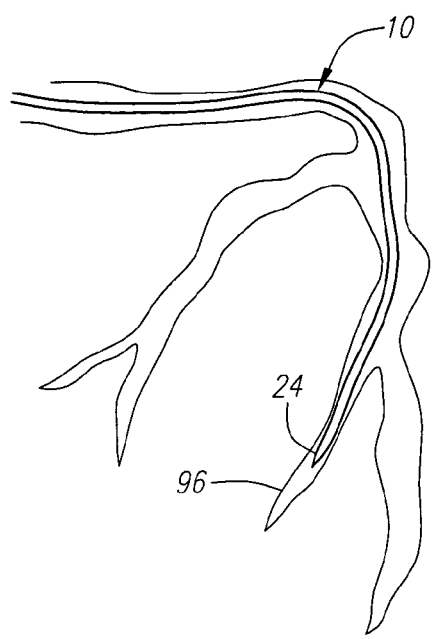
FIGS. 12A-12D are partial cross-sections of a patient's heart, showing a method for delivering an electrical lead into a coronary vein using a sheath apparatus, in accordance with the present invention.

Turning to FIGS. 12A-12D, another method is shown that uses a sheath apparatus 10 (or any of the sheath apparatus described above) for providing access to a target vessel within a patient's vasculature. Specifically, the apparatus 10 may be used to deliver an electrical lead 70, e.g., for a pacemaker, into a coronary vein 96, e.g., adjacent to the left ventricle of the heart. As shown in FIG. 12A, initially, the apparatus 10 may be advanced into the coronary vein 96 with an expandable sheath 20 carried by a stiffening member (not shown) in its contracted condition.

For example, with the sheath 20 collapsed, the apparatus 10 may be introduced from a percutaneous entry site (not shown), e.g., a femoral vein or subclavian vein, and advanced through the patient's venous system into the right atrium of the heart, and into the coronary sinus (not shown) to reach the target coronary vein 96. The apparatus 10 may be advanced over a guidewire (not shown), similar to the previous methods. Because of its relatively low profile, the apparatus 10 may be able to access smaller coronary veins or be advanced further into a target coronary vein than conventional devices.

Once the apparatus 10 is positioned within or near a target vein 96, fluoroscopy and/or other external imaging may be used to facilitate positioning the apparatus 10. The apparatus 10, e.g., the distal end 24 of the sheath 20, an overlying constraint, and the like (not shown), may include one or more radiopaque markers (not shown) to facilitate such imaging. In addition or alternatively, contrast may be introduced into the vein, e.g., via a fluid lumen in a stiffening member (not shown) of the apparatus 10 and/or through the lumen 26 of the sheath 20, to facilitate fluoroscopic imaging. Such imaging may be used to identify the location of the sheath 20 relative to nearby structures, e.g., to ensure that the apparatus 10 is advanced as close as possible to a target location. Preferably, the apparatus 10 is advanced such that the distal end 24 of the sheath 20 is disposed within a coronary vein 96 adjacent the left ventricle of the patient's heart (not shown).

Figure 12B:
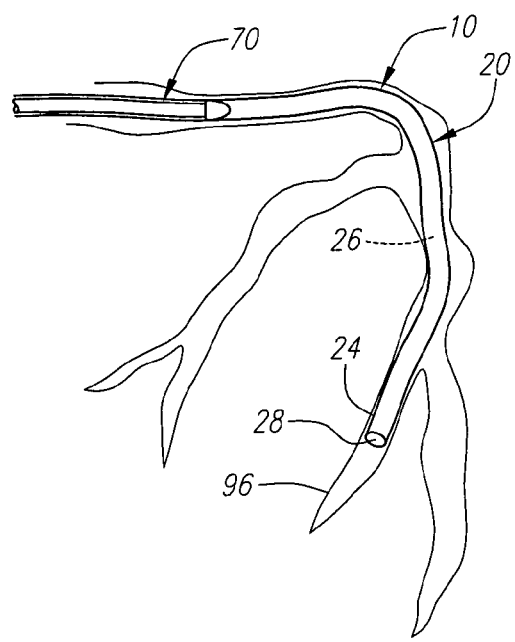

As shown in FIG. 12B, the sheath 20 may be expanded between the entry site and the target vein 96. If a constraint (not shown) is provided, it may be removed before expanding the sheath 20. A fluid, e.g., including saline and/or contrast, may be introduced into the sheath 20 to expand the sheath 20 towards its enlarged condition. Contrast delivered into the sheath 20 may also facilitate imaging the vein 96. For example, if the distal end 24 of the sheath 20 is initially closed, contrast delivered into the lumen 26 may cause the sheath 20 to expand and conform to the shape of the surrounding vessels, thereby facilitating imaging of the vessels through which the sheath 20 is deployed.

Figure 12C:
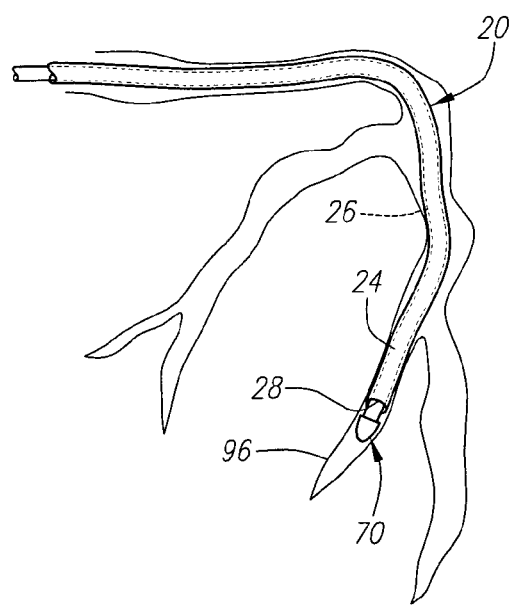

As shown in FIGS. 12B and 12C, an electrical pacing lead 70 may be advanced through the lumen 26 of the sheath 20 until a tip 72 of the lead 70 is disposed within the target vein 96. Similar to the methods described above, the sheath 20 may already include an opening 28 in its distal end 24 that communicates with the lumen 26 or an opening may be created in a closed sheath distal end 24 (not shown). The tip 72 may be deployed from the sheath 20, e.g., by retracting the sheath 20 or advancing the tip 72 through the opening 28 beyond the distal end 24 of the sheath 20, thereby substantially anchoring the tip 72 within the vein 96.

Figure 12D:
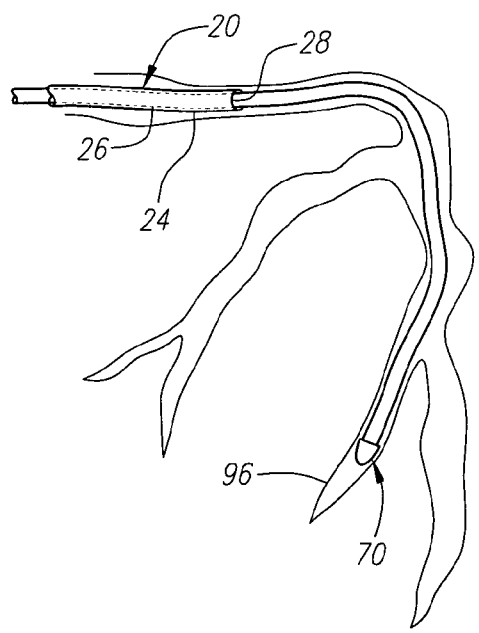

As shown in FIG. 12D, the sheath 20 may then be removed from the vein 96 and from the patient's vasculature. Preferably, the sheath 20 may be split into one, two, or more pieces to allow the sheath 20 to be removed easily from around the lead 70. Implantation of the lead 70 may then be completed using conventional methods.

Turning to FIGS. 14A-14C, another method is shown for delivering a colonoscope 76 into a patient's colon 98 using a sheath apparatus 10, such as any of the embodiments described above. As shown in FIG. 14A, the apparatus 10 is advanced into the colon 98 with the sheath 20 in its contracted condition. Once advanced to a desired location, the sheath 20 may be expanded to an enlarged condition to define a lumen 26, as shown in FIG. 14B. The colonoscope 76 may be advanced through the lumen 26 of the sheath 20, similar to the previous embodiments. If desired, the sheath 20 may be configured such that the colonoscope 76 may image surrounding tissue within the colon 76 as the colonoscope 76 is advanced through the sheath 20. For example, the material of the sheath 20 may be substantially transparent to visible light (or other portions of the spectrum) that is used by the colonoscope 76. Alternatively, in other applications, the sheath 20 may allow other imaging sources, e.g., ultrasound energy, to pass substantially freely through the sheath 20 to allow imaging of the surrounding tissue. The sheath 20 may be removed from around the colonoscope 76, as shown in FIG. 14C, or may remain at least partially around the colonoscope 76, e.g., to facilitate its removal after a procedure. In addition, the sheath 20 may be adapted for introducing fluid, e.g., air, carbon dioxide and the like, into the gastrointestinal lumen.

Figure 15A:
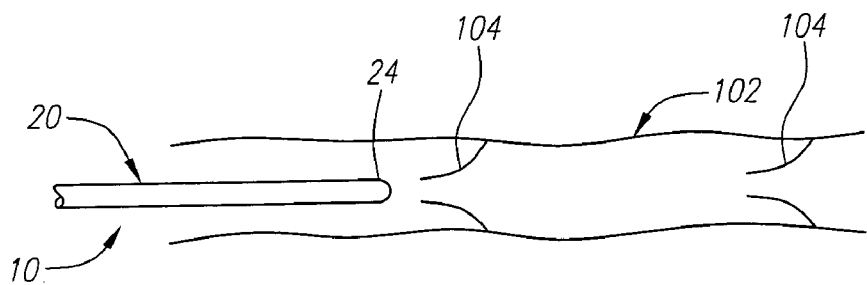
FIGS. 15A-15D are partial cross-sectional views of a vein, showing a method for delivering a stent through valves of the vein.
Figure 15B:
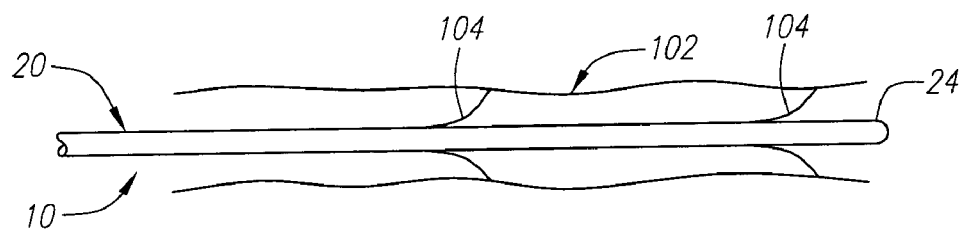
Figure 15C:
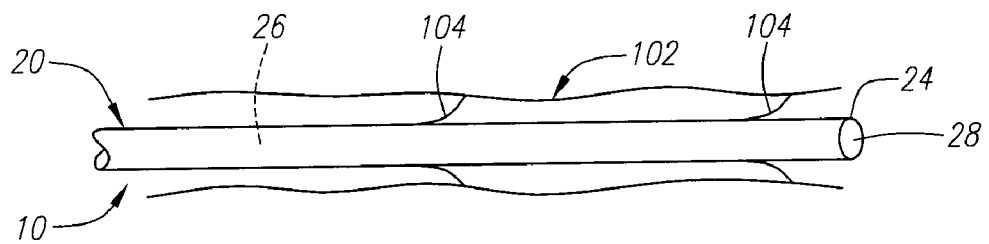
Figure 15D:
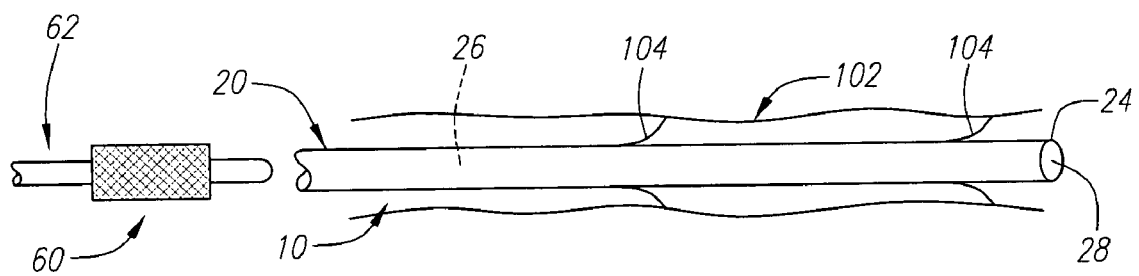
Figure 16:
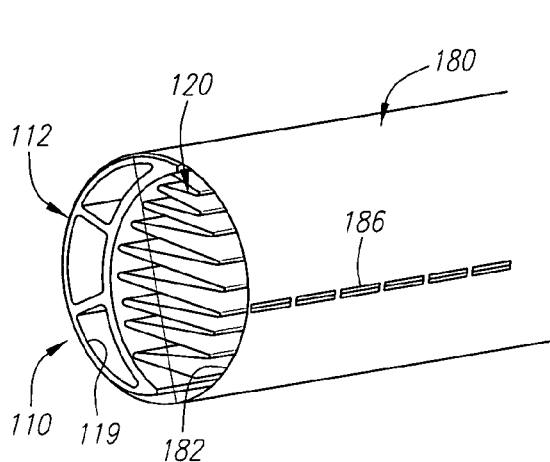
FIGS. 16A-16C are perspective details of another embodiment of a sheath apparatus including an outer sheath that may separate to accommodate expansion of an expandable sheath therein.

Turning to FIGS. 15A-15D, a sheath apparatus in accordance with the present invention may facilitate advancement of one or more instruments retrograde into a patient's venous system. For example, as shown in FIG. 15A, an exemplary vein 102 is shown that includes a plurality of valves 104. A sheath apparatus 10 (which may be any of the embodiments described herein) may be advanced into the vein 102 with an expandable sheath 20 in its contracted condition, as shown in FIG. 15B. Once advanced to a desired position, the sheath 20 may be expanded to its enlarged condition, as shown in FIG. 15C, thereby opening the valves 104 and provided a relatively large bore lumen 26 through the vein 102. One or more instruments, such as the stent 60 and catheter 60 shown in FIG. 14D, may be advanced through the lumen 26 to complete a procedure, similar to the embodiments described above.

A sheath apparatus according to the present invention may also be used to perform other diagnostic and/or therapeutic procedures within the vasculature. For example, the apparatus may provide an expandable lumen for delivering an imaging element, e.g., an intravascular ultrasound ("IVUS") device, endoscope, fiber optic element, and the like, and/or for delivering therapeutic instruments, e.g., angioplasty catheters, stent delivery devices, atherectomy or thrombectomy devices, and the like.

In alternative methods, a sheath apparatus in accordance with the present invention may be used to provide access and/or deliver instruments to other body lumens within a patient's body. For example, the apparatus may be used within a patient's urogenital tract, respiratory tract, gastrointestinal tract, lymphatic system, or vascular system. In addition, the apparatus may be introduced into surgically created openings and advanced into surgically created passageways, e.g., a passageway created within interstitial space, e.g. to obtain a biopsy.

Turning to FIGS. 18 and 19A-19C, another embodiment of a sheath apparatus 510 is shown, in accordance with the present invention. Generally, the apparatus 510 includes a catheter or other elongate member 512 and an expandable sheath 520. The catheter 512 may be an elongate tubular body formed from uniform or variable flexibility material, e.g., having a substantially flexible distal end 514. The catheter 512 may include one or more lumens (not shown) extending from its proximal end (also not shown) to the distal end 514.

In a preferred embodiment, the catheter 512 includes one or more diagnostic or therapeutic elements 516 on the distal end 514. For example, the catheter 512 may include an imaging element, such as an intravascular ultrasound ("IVUS") device, and the like, and/or a dissection element, such as a cutting or ablation element, e.g., for observing and/or treating an occlusion within a blood vessel (not shown). In addition or alternatively, the catheter 512 may include a steering element (also not shown) for manipulating the distal end 514 within a patient's body.

The sheath 520 may be a substantially flexible, and preferably flimsy, membrane or other structure. For example, the sheath 520 may include any of the materials and/or structures included in any of the embodiments described previously. The sheath 520 may be substantially permanently attached to an outer surface 518 of the catheter 512. For example, the sheath 520 may include a sheet whose longitudinal edges are attached at one or more locations along a length of the catheter 512. Alternatively, the sheath 520 may be a tubular member having an outer surface that is attached at one or more locations along the length of the catheter 512. Thus, the sheath 520 may extend at least partially between the proximal end and the distal end 514 of the catheter 512.

The sheath 520 may be expandable from a contracted condition (shown in FIG. 19A), e.g., to minimize a profile of the sheath 520, and an enlarged condition (shown in FIGS. 19B and 19C). In the enlarged condition, the sheath 520 may at least partially define an accessory lumen 522. The accessory lumen 522 may extend between a proximal end (not shown)

and a distal end 524 of the sheath 520, preferably terminating adjacent the distal end 514 of the catheter 512.

The distal end 524 of the sheath 520 may include an opening (not shown) communicating with the accessory lumen 522. Alternatively, the distal end 524 may be closed, and may include a break-away portion for creating an opening (not shown) such that an instrument (such as a guidewire 580, shown in FIG. 19C) inserted through the lumen 522 may be advanced from the opening into a body lumen, similar to the previous embodiments.

Optionally, a constraint (not shown) may be provided for maintaining the sheath 520 in the contracted condition, e.g., as the apparatus 510 is advanced through a patient's body. For example, an outer sheath (not shown) may be provided for receiving the catheter 512 and the sheath 520) that may be removed before the sheath 520 is expanded. In addition or alternatively, an adhesive may be used to temporarily secure the sheath 520 along the outer surface 518 of the catheter 512. Thus, the adhesive may retain the sheath 520 substantially flat along the outer surface 518 of the catheter 512, as shown in FIG. 19A. The adhesive may release when internal pressure is delivered into the lumen 522 of the sheath 520 or may dissolve within a body lumen to release the sheath 520 to allow the sheath 520 to expand.

Turning to FIGS. 20A-20D, a method is shown for delivering an instrument, e.g., a guidewire 580 through a total occlusion 592, e.g., within a blood vessel or other body lumen 590, e.g., using the apparatus 510 shown in FIG. 18. Initially, as shown in FIG. 20A, with the sheath 520 in its contracted condition, the apparatus 510 may be introduced into the vessel 590, e.g., via a percutaneous entry site (not shown), until the distal end 514 of the catheter 512 is located proximally (e.g., upstream) relative to the occlusion 592.

With reference to FIG. 20B, the distal end 514 of the catheter 512 may be advanced through the occlusion 592 until the distal end 524 of the sheath 520 is disposed distally (e.g., downstream) relative to the occlusion 592. The catheter 512 may include one or more elements 516 on the distal end 514 for facilitating advancing the catheter 512 through the occlusion 592. For example, the catheter 512 may carry an imaging element, e.g., an IVUS device (not shown), on the distal end 514 for imaging the occlusion. In addition or alternatively, a dissection element, e.g., a cutting, core, and/or ablation element (not shown), may be provided on the distal end 514 for creating a passage 594 through the occlusion. Optionally, the catheter 512 may include a steering element (not shown) to facilitate manipulating the distal end 514 of the catheter 512 as it is advanced through the occlusion 592.

Once the sheath 520 extends through the occlusion 592, an elongate member, e.g., a guidewire 580 or other instrument (not shown), may be inserted through the sheath 520 until a distal end 582 of the guidewire 580 is disposed distal to the occlusion 592. The sheath 520 may be expanded as the guidewire 580 or other instrument is advanced through the sheath 520. Alternatively, the sheath 520 may be dilated, e.g., by introducing a fluid into the lumen 522 of the sheath 520, similar to the embodiments described above.

The apparatus 510 may then be withdrawn through the occlusion 592 and/or out of the vessel 590. One or more instruments (not shown) may then be advanced over the guidewire 592, e.g., to treat the occlusion 592 and/or to deliver agents or fluids distally beyond the occlusion 592, as is well known to those skilled in the art. Thus, unlike the previous embodiments, the sheath 520 may provide a lumen for a secondary device, e.g., a guidewire, that may be delivered in cooperation with the catheter 512.

Figure 25A:
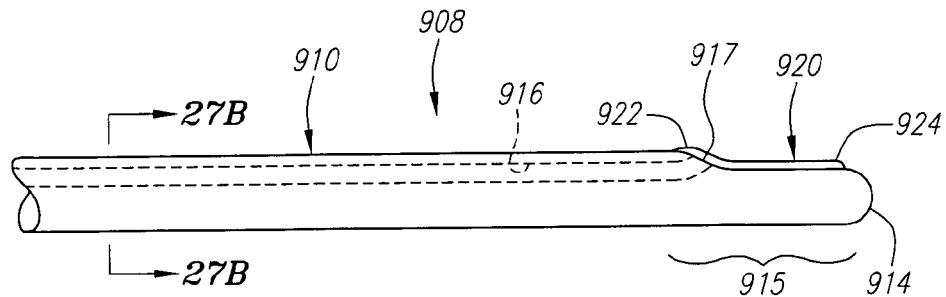
FIGS. 25A-25C are side views of a distal end of a catheter including an expandable sheath attached to an outer surface of the catheter for receiving a guidewire or other instrument therethrough.
Figure 25B:
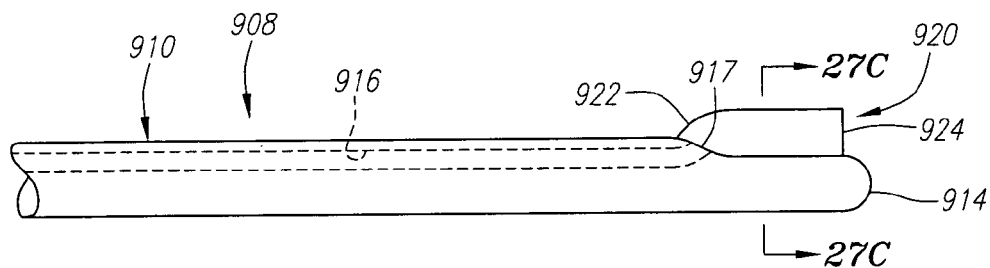
Figure 25C:
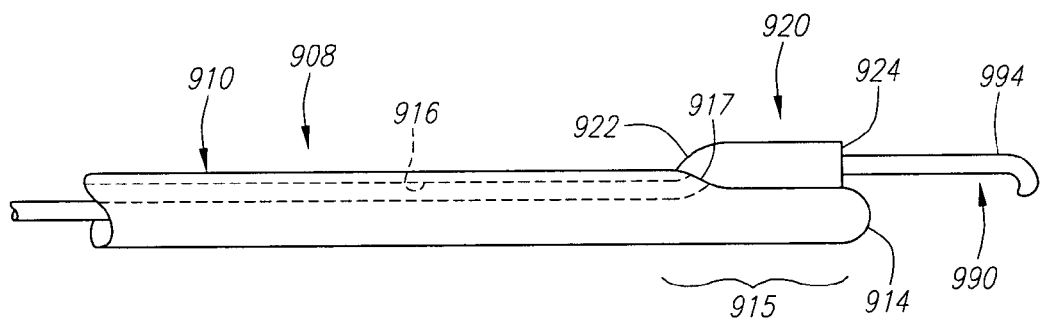

Turning to FIGS. 25A-25C, another embodiment of an apparatus 908 is shown for delivering an instrument, e.g., a guidewire 990, and/or agents (not shown) into a body lumen of a patient, e.g., across a total occlusion within a blood vessel (not shown). Generally, the apparatus 908 includes a catheter or other elongate and/or tubular member 910 including a proximal end (not shown), a distal end 914 sized for insertion into a body lumen, and a first lumen 916 extending from the proximal end to a distal region 915 of the catheter 910.

As shown, the first lumen 916 terminates in an outlet port or side opening 917 on the distal region 915 proximal to the distal end 914. In an exemplary embodiment, the opening 917 may be located at least about five to fifty millimeters (5-50 mm) from the distal end 914. The opening 917 may be oriented transversely, e.g., substantially perpendicular to a longitudinal axis of the catheter 910. Alternatively, the opening 917 may be oriented laterally or even axially, e.g., if the outer surface of catheter 910 is tapered along the distal region 915, as described further below.

Optionally, the catheter 910 may include one or more additional lumens. For example, as shown in FIGS. 27A-27C, the catheter 910 may include a second lumen 918 extending between the proximal end and the distal end 914 of the catheter 910. Alternatively, the catheter 910 may include one or more additional lumens (not shown) for various purposes, such as an inflation lumen for an expandable member (not shown) carried by the catheter, e.g., for occlusion, dilation, and/or distal protection, similar to the other embodiments described herein. In another alternative, the catheter 910 may include the first lumen 916 and the second lumen 918 may be eliminated, e.g., such that the distal region 915 does not include a lumen therein.

The catheter 910 may be formed from one or more segments, e.g., multiple tubular segments having different materials and/or shapes. For example, as shown in FIGS. 25A-25C and 27C, the distal region 915 may be a tubular member including a single lumen 918, while, as shown in FIGS. 25A-25C and 27B, an intermediate region of the catheter 910 (i.e., proximal to the distal region 915) may be a tubular member including two lumens 916, 918, e.g., disposed adjacent one another. Thus, the distal region 914 may have a diameter or other cross-section that is substantially smaller than the remainder of the catheter 910. Optionally, the catheter 910 may include a taper or other reduction between the intermediate region and the distal region 915, e.g., to provide a substantially atraumatic transition.

An expandable sheath 920 is provided on the distal region 915 of the catheter 910 that is expandable from a contracted condition (as shown in FIG. 25A), to an enlarged condition (as shown in FIGS. 25B and 25C). The contracted condition may minimize a profile of the sheath 920, e.g., to facilitate inserting the sheath 920 along with the catheter 910 through a patient's vasculature or other body lumen. In the enlarged condition, the sheath 920 may at least partially define a lumen 928 communicating with the first lumen 916 of the catheter 910.

The sheath 920 may be formed from a flexible and/or flimsy tubular member and/or sheet, similar to the other embodiments described herein. For example, with additional reference to FIG. 27A, the expandable sheath 920 may be constructed using a dual lumen body 950, e.g., including two adjacent tubular bodies 952, 954 connected along their lengths. The tubular bodies 952, 954 may be extruded simultaneously through a single tool, as is known in the art. Alternatively, a single lumen tubular body (not shown) may be extruded or otherwise formed, and the tubular body may be pressed together to form the dual lumen body 950. In a further alternative, the dual lumen body 950 may be formed from one or more sheets whose longitudinal edge(s) may be bonded, sonic welded, or otherwise attached to one another to form the dual lumen body 950.

One of the tubular bodies, e.g., tubular body 952, may be placed over the distal region 915 of the catheter 910. The tubular body 952 may be bonded or otherwise attached to the outer surface of the catheter 910, e.g., using an adhesive, heat bonding, solvent bonding, mechanical interference, and the like, alone or in combination. For example, the dual lumen body 950 may be formed from a heat-shrinkable material, e.g. PET, polyolefin, PTFE, and the like. At least the tubular body 952 may be expanded such that the original size may be recovered by application of heat from a larger diameter to a smaller diameter.

Thus, in one embodiment, the tubular body 952 may be expanded, placed over the distal region 915 of the catheter 910, and heated to cause the tubular body 952 to shrink to fit tightly around the catheter 910. The other tubular body 954 may then provide the sheath 920, defining lumen 926 extending along the catheter 910, e.g., along the exterior surface of the distal region 915.

Alternatively, a thin strip or sheet of material (not shown) may be wrapped around the catheter 910 and bonded or otherwise secured, e.g., using an adhesive, heat shrinking, and the like. In addition or alternatively, it will be appreciated that more than two lumens (not shown) may be created in similar fashions, e.g. a triple lumen extrusion may be created provide two expandable sheath lumens extending along at least the distal region of the catheter.

The proximal end 922 of the sheath 920 may be closed and/or sealed such that the lumen 926 of the sheath 920 communicates with the first lumen 916 of the catheter 910. For example, the proximal end 922 may be bonded to the outer surface of the catheter 910 around the opening 917. The distal end 924 of the sheath 920 may remain open or may be tearable or penetrable, similar to other embodiments described herein.

To retain the sheath 920 in the contracted condition, the sheath 920 may be bonded or otherwise constrained against the outer surface of the catheter 910 such that the sheath 920 may be at least partially separated from the catheter 910 to expand towards the enlarged condition.

Turning to FIGS. 25B and 25C, the expandable sheath 920 may be expanded towards the enlarged condition by introducing an instrument, e.g. a guide wire 990, or fluid, e.g. saline, into the first lumen 916 of the catheter 910. For example, as shown in FIG. 25C, distal end 994 of guidewire 990 may be inserted into the first lumen 916 from the proximal end of the catheter 910. The distal end 994 of the guidewire 990 may be advanced through the first lumen 916, out the opening 917 into the lumen 926 of the sheath 920 and out the distal end 924 of the sheath 920.

Figure 26:
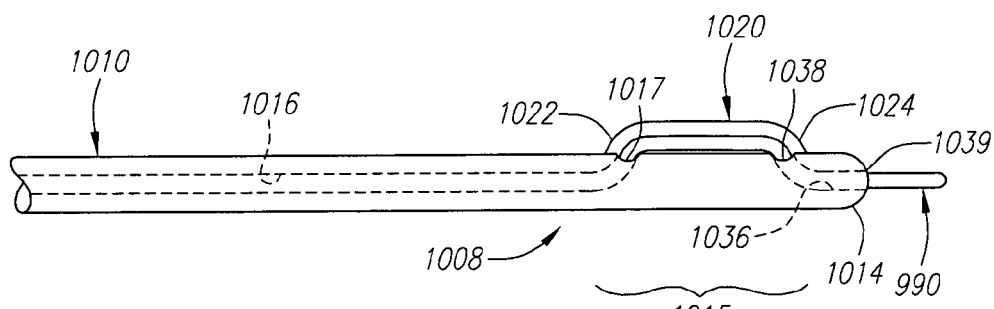
FIG. 26 is a side view of a distal end of another embodiment of a catheter including an expandable sheath.

Turning to FIG. 26, an alternative embodiment of an apparatus 1008 is shown that includes a catheter 1010 carrying an expandable sheath 1020 on a distal region 1015 thereof, similar to the previous embodiments. The catheter 1010 is a tubular member including a first lumen 1016 extending from a proximal end to a first opening 1017 in the distal region 1015. Unlike the previous embodiments, the catheter 1010 includes a distal passage or lumen 1036 that extends distally from an inlet port or second side opening 1038. The second opening 1038 may be located distal to the first opening 1017, e.g., between the first opening 1017 and the distal end 1014, and may extend to a third opening 1039 in the distal end 1014 of the catheter 1010.

The sheath 1020 may be attached to the distal region 1015 of the catheter 1010 such that a proximal end 1022 of the sheath 1020 communicates with the first opening 1017 and a distal end 1024 of the sheath 1020 communicates with the second opening 1038. Thus, a guidewire 990 advanced into the first lumen 1016 may exit the first opening 1017, pass through the sheath 1020, enter the second opening 1038, and pass through the passage 1036 until it exits the third opening 1039 and is advanced distally beyond the distal end 1014 of the catheter 1010.

Similar to the previous embodiments, this embodiment may allow the diameter or other cross-section of the distal region 1015 of the catheter 1010 to be reduced, e.g., while the lumen 1026 defined by the sheath 1020 is not in use. When needed, e.g., after crossing through a partial or complete occlusion, the sheath 1020 may be expanded and/or collapsed, as needed to provide a lumen through the occlusion.

Turning to FIGS. 28A-28D, alternative embodiments of an apparatus including a catheter and expandable sheath are shown that may be provided instead of the embodiments described above. For example, FIG. 28A shows a cross-section of a catheter 910' that includes a strip or thin film 920' that is attached along opposite edges 921' thereof to the catheter 910.' The edges 921' may be attached continuously or intermittently between proximal and distal ends of the sheath 921' so as to create an effective path to guide an instrument, e.g. a guidewire, being introduced therethrough.

FIG. 28B shows another construction of an apparatus 908" that includes a tubular sheath material, e.g., made from a thin and/or flexible sheet or tube, that is placed over catheter 910" to provide an expandable sheath 920." A thin "C" shaped retaining structure 950," e.g., a tubular member in which a longitudinal slit 952" is created along one side, is placed over the sheath material with a small loop extending through the slit 952" to define an expandable sheath 920." The retaining structure 950" may be constructed from a relatively rigid material, e.g. polyimide and the like, so as to hold itself in place. In addition or alternatively, the retaining structure 950" may be bonded continuously or intermittently along its length and/or otherwise attached to the sheath material and/or catheter 910." Bonding or other attachment to the catheter 91o" may be facilitated by providing perforations in the sheath material, thereby allowing the retaining structure 950" to be attached directly to the exterior surface of the catheter 910." The retaining structure 950" may be a substantially continuous length extending between the proximal and distal ends of the catheter 910" or multiple, relatively short segments, e.g., with at least two segments bonded at the proximal and distal ends of the catheter 910" to hold the sheath material in place.

Turning to FIG. 28C, another embodiment is shown in which a tubular sheath 920'" is attached to the exterior surface of a catheter 910.'" The sheath 920'" is shown in its contracted condition, which may involve temporarily constraining the sheath 920'" in the contracted condition, e.g. by vacuum, by adhesive, coatings, heat forming, and the like. Alternatively, the sheath material may be sufficiently thin and flexible such that the sheath 920'" tends to lie substantially flat against the exterior surface of the catheter 910'" and/or deflects without substantial resistance when encountering objects during introduction or other placement of the catheter 910.'"

Turning to FIG. 28D, yet another construction for a catheter 910"" and expandable sheath 920"" are shown. The sheath 920"" includes a single lumen tubular body, e.g., formed from relatively thin and/or flexible material, that extends along the catheter 910"" on its distal region 915"" or, optionally, between proximal and distal ends of the catheter 910."" The tubular body may be bonded or otherwise attached to the catheter 910"" longitudinally, e.g., by a bond that extends over at least part of the exterior surface of the catheter 910"" and the sheath 920."". The attachment points between the sheath 920"" and the catheter 910"" may be substantially continuous or intermittent, with at least two attachment points, one at the proximal end and one at the distal end of the sheath 920."".

Any of these apparatus just described may be used to access a body lumen, e.g., for crossing a partial or total occlusion within a blood vessel, similar to the embodiments described above. Because the distal region of the catheter includes an expandable sheath that is initially collapsed, the profile of the distal region may be minimized, which may facilitate advancing the distal region through the occlusion. Once the distal region of the catheter has crossed the occlusion, the sheath may be expanded, e.g., by advancing a guidewire through the catheter and sheath, or a source of saline or other inflation media may be coupled to the catheter and fluid may be delivered into the sheath to expand it. With a guidewire positioned across the occlusion, the catheter and sheath may be removed and other devices, e.g., dilation catheter and the like (not shown) may be advanced over the guidewire into and/or through the occlusion to treat the occlusion and/or the vessel beyond the occlusion.

Figure 29A:
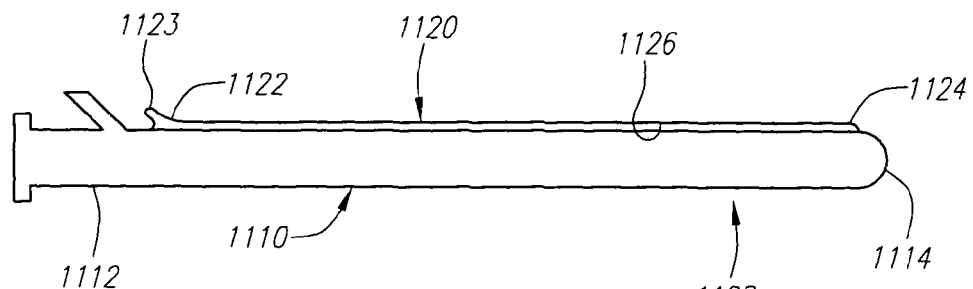
FIGS. 29A-29C are side views of still another embodiment of a catheter including an expandable sheath attached to an outer surface of the catheter for receiving a guidewire or other instrument therethrough.
Figure 29B:
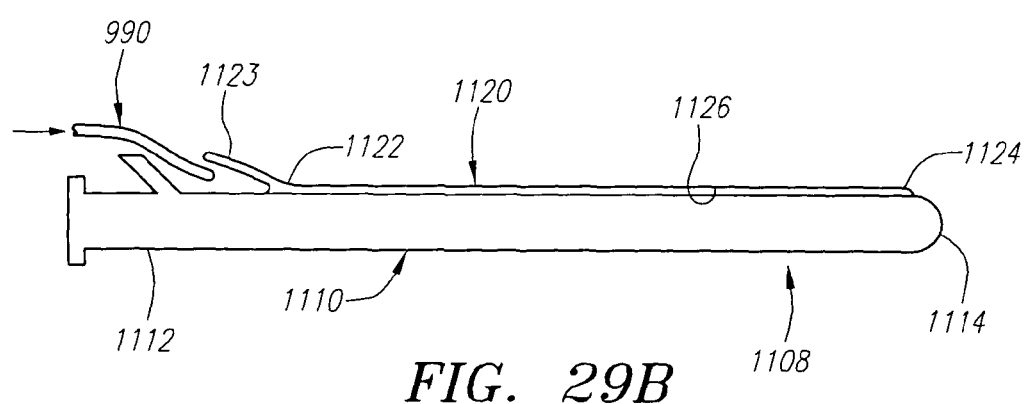
Figure 29C:
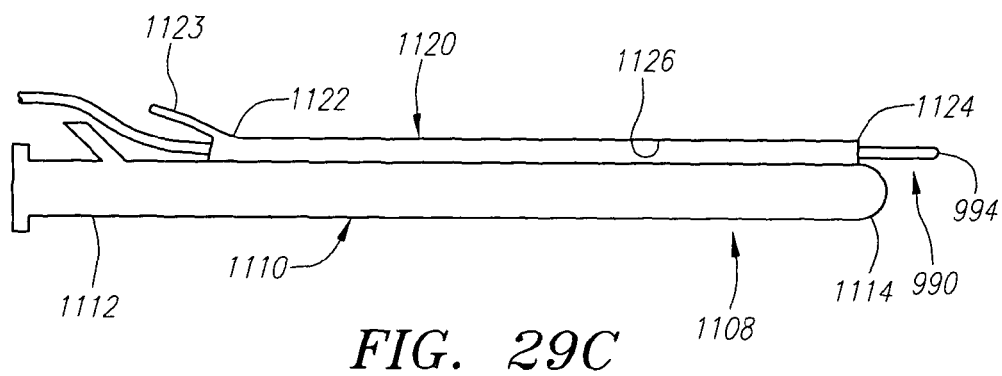

Turning to FIGS. 29A-29C, another embodiment of an apparatus 1108 is shown that includes a catheter 1110 carrying an expandable sheath 1120 that extends substantially along the entire length of the catheter 1110. As shown, a proximal end 1122 of the sheath 1120 may include one or more tabs 1123 extending from the sheath 1120. The tab(s) 1123 may be pulled away from the exterior surface of the catheter 1110, e.g., transversely away from the catheter 1110 to at least partially separate the sheath 1120 from the catheter 1110 and begin to open the proximal end 1122 of the sheath 1120. This may facilitate inserting an instrument, e.g. a guidewire 990 (shown in FIG. 29C) through the lumen 1126 of the sheath 1120. FIG. 29B shows a distal end 994 of the guidewire 990 being inserted into the proximal end 1122 and advanced through the sheath 1120, separating and/or expanding the sheath 1120. FIG. 29C shows the guidewire 990 fully inserted through the lumen 1126 of the sheath 1120.

Figure 30:
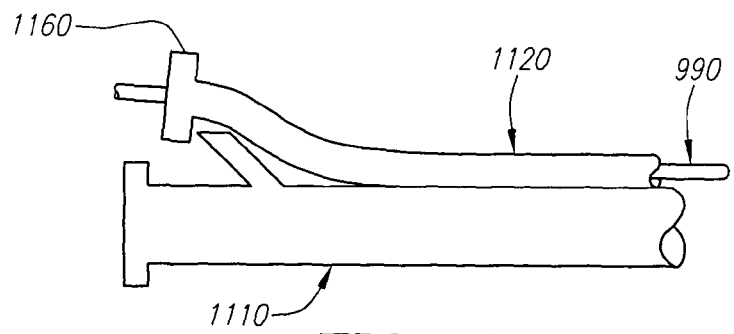
FIG. 30 is a detail of the proximal end of the catheter of FIGS. 29A-29C.

The proximal end 1122 of the sheath 1120 may take a variety of configurations and/or shapes, e.g., to facilitate inserting an instrument or delivering fluid or other inflation media from a source into the lumen 1126 of the sheath 1120. FIG. 30 is a detail of the proximal end of the apparatus 1108, including an optional proximal adapter 1160 on the sheath 1120 configured to create a hermetic seal around the guidewire or other instrument inserted into the sheath 1120, such as a Toughy-Borst valve and the like. Optionally, the proximal adapter 1160 may be a luer fitting or other standard proximal fitting (not shown), e.g., to enable and/or facilitate device insertion, fluid infusion, sealing, and the like.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for delivering a guidewire through an occlusion in a body lumen, comprising:
   a catheter extending from a proximal end thereof to a distal end thereof, the catheter including a lumen, an intermediate region, a distal region, and a taper between the intermediate region and the distal region such that the distal region has a smaller cross-section than the intermediate region, the lumen of the catheter extending distally from the proximal end and through the intermediate region to terminate in an outlet port located on a sidewall of the catheter in proximity to the taper and no greater than approximately 50mm from the distal end of the catheter, and the distal region extending distally from the outlet port to the distal end of the catheter; and
   two adjacent tubular bodies connected together along their lengths, a first of the tubular bodies being fitted tightly around and attached to the catheter along an exterior surface of the distal region thereof, and a second of the tubular bodies forming an entirety of an expandable sheath, the sheath being expandable from a contracted condition to an enlarged condition, at which enlarged condition the sheath defines a sheath lumen that extends along the exterior surface of the distal region of the catheter around which the first tubular body is tightly fitted, the sheath including a proximal end and a distal terminal end, the proximal end of the sheath being bonded around the outlet port of the lumen of the catheter, such that the sheath lumen communicates therewith, and the distal terminal end of the sheath being separable from the distal region of the catheter, when the sheath is expanded to the enlarged condition, such that the distal terminal end of the sheath surrounds and defines a distal opening of the sheath lumen, the distal opening being located proximal to the distal end of the catheter and facing toward the distal end.

2. The apparatus of claim 1, further comprising a guidewire insertable through the lumen of the catheter and into the sheath lumen, thereby expanding the sheath to accommodate advancing the guidewire therethrough and out the distal opening of the sheath lumen.

\* \* \* \* \*